United States Patent
Hollender et al.

(10) Patent No.: US 10,959,703 B2
(45) Date of Patent: Mar. 30, 2021

(54) METHODS, SYSTEMS AND COMPUTER PROGRAM PRODUCTS FOR SINGLE TRACK LOCATION SHEAR WAVE ELASTICITY IMAGING

(71) Applicant: DUKE UNIVERSITY, Durham, NC (US)

(72) Inventors: Peter J. Hollender, Durham, NC (US); Gregg E. Trahey, Durham, NC (US)

(73) Assignee: Duke University, Durham, NC (US)

( * ) Notice: Subject to any disclaimer, the term of this patent is extended or adjusted under 35 U.S.C. 154(b) by 256 days.

(21) Appl. No.: 15/574,047

(22) PCT Filed: Jun. 1, 2016

(86) PCT No.: PCT/US2016/035263
§ 371 (c)(1),
(2) Date: Nov. 14, 2017

(87) PCT Pub. No.: WO2016/196631
PCT Pub. Date: Dec. 8, 2016

(65) Prior Publication Data
US 2018/0296189 A1 Oct. 18, 2018

Related U.S. Application Data

(60) Provisional application No. 62/169,073, filed on Jun. 1, 2015.

(51) Int. Cl.
| | |
|---|---|
| *A61B 8/08* | (2006.01) |
| *G01N 29/07* | (2006.01) |
| *G01N 29/04* | (2006.01) |
| *G01N 29/06* | (2006.01) |
| *A61B 8/00* | (2006.01) |

(Continued)

(52) U.S. Cl.
CPC .............. *A61B 8/485* (2013.01); *A61B 8/463* (2013.01); *A61B 8/466* (2013.01); *A61B 8/5207* (2013.01);

(Continued)

(58) Field of Classification Search
CPC ....... A61B 8/485; A61B 8/463; A61B 8/5207; A61B 8/5223; G01S 7/52085;
(Continued)

(56) References Cited

U.S. PATENT DOCUMENTS

| 6,764,448 B2 | 7/2004 | Trahey et al. |
| 8,118,744 B2 | 2/2012 | Palmeri et al. |

(Continued)

OTHER PUBLICATIONS

International Search Report and Written Opinion for PCT/US2016/035263 dated Aug. 31, 2016, 11 pages.

(Continued)

*Primary Examiner* — Herbert K Roberts
*Assistant Examiner* — John M Royston
(74) *Attorney, Agent, or Firm* — Myers Bigel, P.A.

(57) ABSTRACT

Methods, systems and computer program products for determining a mechanical parameter for a sample having a target region using shear wave displacement are provided. The method includes a) generating at least one shear wave with an excitation pulse in the target region at an excitation position; b) transmitting tracking pulses in a tracking region, at least a portion of which is outside the target region; c) receiving corresponding echo signals for the tracking pulses in the tracking region; d) repeating steps A through C for one or more additional excitation positions within the target region, wherein at least two of the excitation pulses overlap and the tracking region associated with each excitation position overlaps with the tracking region associated with at least one other excitation position; and e) determining at least one mechanical parameter of the target region based on at least one parameter of a shear wave displacement.

25 Claims, 16 Drawing Sheets

(51) Int. Cl.
*G01S 7/52* (2006.01)
*G01N 29/09* (2006.01)
*G01S 15/89* (2006.01)

(52) U.S. Cl.
CPC .......... *A61B 8/5223* (2013.01); *G01N 29/043* (2013.01); *G01N 29/0654* (2013.01); *G01N 29/07* (2013.01); *G01N 29/09* (2013.01); *G01S 7/52022* (2013.01); *G01S 7/52042* (2013.01); *G01S 7/52085* (2013.01); *G01N 2291/02475* (2013.01); *G01N 2291/02827* (2013.01); *G01N 2291/106* (2013.01); *G01S 7/52047* (2013.01); *G01S 15/8915* (2013.01)

(58) Field of Classification Search
CPC ............ G01S 7/52042; G01S 7/52022; G01S 7/52047; G01S 15/8915; G01N 29/09; G01N 29/0654; G01N 29/043; G01N 29/07; G01N 2291/106; G01N 2291/02827; G01N 2291/02475
See application file for complete search history.

(56) References Cited

U.S. PATENT DOCUMENTS

| | | |
|---|---|---|
| 2010/0286520 A1 | 11/2010 | Hazard et al. |
| 2011/0184287 A1 | 7/2011 | McAleavey |
| 2012/0116220 A1 | 5/2012 | Burcher et al. |
| 2012/0123262 A1* | 5/2012 | Xie ...................... A61B 5/0048 600/438 |
| 2013/0237820 A1* | 9/2013 | Vappou .................. A61B 8/485 600/438 |
| 2014/0148698 A1 | 5/2014 | Tamano |
| 2016/0345939 A1* | 12/2016 | Toji ........................ A61B 8/485 |

OTHER PUBLICATIONS

Rouze, Ned C., et al., "Parameters Affecting the Resolution and Accuracy of 2-D Quantitative Shear Wave Images," IEEE Transactions on Ultrasonics, and Frequency Control, vol. 59, No. 8, Aug. 2012, pp. 1729-1740.

Nightingale, Kathryn, et al, "Shear-Wave Generation Using Acoustic Radiation Force: In Vivo and Ex Vivo Results," Ultrasound in Med. & Bio., vol. 29, No. 12, 2003, pp. 1715-1723.

Hollender, Peter J., et al., "Single- and Multiple-Track-Location Shear Wave and Acoustic Radiation Force Impulse Imaging: Matched Comparison of Contrast, Contrast to Noise Ratio and Resolution," Ultrasound in Med. & Bio., vol. 41, No. 4, 2015, pp. 1043-1057.

Extending European Search Report for EP Application No. 16804239.7 dated Jan. 29, 2019, 11 pages.

* cited by examiner

METHODS, SYSTEMS AND COMPUTER PROGRAM PRODUCTS FOR SINGLE TRACK LOCATION SHEAR WAVE ELASTICITY IMAGING

RELATED APPLICATIONS

This application is a 35 U.S.C. § 371 national stage application of PCT International Application No. PCT/US2016/035263, filed Jun. 1, 2016 which claims priority to U.S. Provisional Application 62/169,073, filed Jun. 1, 2015, the disclosures of which are hereby incorporated by reference in their entireties.

STATEMENT OF GOVERNMENT SUPPORT

This invention was made with government support under Grant No. R37H1096023 awarded by the National Institutes of Health. The government has certain rights in the invention.

FIELD OF THE INVENTION

The present invention relates to ultrasound imaging and analysis, and in particular, to determining mechanical parameters of a sample from a set of generated shear waves at a tracking location.

BACKGROUND

Acoustic Radiation Force (ARF) shear wave elasticity imaging methods typically use a transverse propagation velocity of mechanical shear waves in materials to estimate mechanical properties of a sample, such as material elasticity constants. These techniques may be adapted into imaging systems to compute the local shear wave propagation velocity as a function of both axial and lateral position. The velocity may be calculated by estimating the differences in arrival times of the shear waves, either at different recording locations or from different excitation locations.

For example, acoustic radiation force (ARF) arises from a transfer of momentum from a sound wave to the medium through which it is traveling due to both absorption and scattering of the wave and is described by K. R. Nightingale, M. Palmeri, R. Nightingale, and G. Trahey, "On the feasibility of remote palpation using acoustic radiation force," J Acoust Soc Am, vol. 110, pp. 625-634, 2001 and G. R. Torr, "The Acoustic Radiation Force," Am. J. Phys., vol. 52, pp. 402-408, 1984.

$$\vec{F} = \frac{2\alpha \vec{I}}{c} \quad (1)$$

where $\alpha$ is the acoustic attenuation, I is the acoustic intensity, c is the speed of sound, and F is the force applied to the medium. Ultrasonic Shear Wave Elasticity Imaging (SWEI) utilizes this acoustic radiation force by applying ultrasonic pushing pulses that displace the tissue on the order of microns and tracking the propagation of the transverse wave that propagates away from the region of excitation.

SWEI is currently used to characterize the stiffness of tissues, including liver fibrosis. Initial implementations of SWEI involved using sparse displacement fields in inverted wave equation solutions, or time-of-flight algorithms, in which shear wave arrival times are estimated at multiple spatial locations with an assumed direction of propagation. See M. L. Palmeri, M. H. Wang, J. J. Dahl, K. D. Frinkley, K. R. Nightingale, and L. Zhai "Quantifying Hepatic Shear Modulus In Vivo Using Acoustic Radiation Force. Accept. UMB, 34(4):546-558 (April 2008). Additional improvements to SWEI include using multiple shear wave sources that can create a unique shear wave morphology that can be tracked at a single location using correlation-based methods, with the benefit of reduced shear wave speed estimation variance. See U.S. Pat. No. 8,225,666 and U.S. Patent Publication No. 2011/0184,287, the disclosures of which are hereby incorporated by reference in their entireties.

Currently used SWEI techniques that utilize acoustic radiation force to generate shear waves typically require diagnostic ultrasound arrays to generate and track shear waves, with significant signal processing overhead to calculate shear wave arrival times and to estimate shear wave speeds.

U.S. Pat. Nos. 8,753,277 and 8,225,666 to McAleavey discuss a spatially-modulated source function to estimate shear velocity from a single recording location, and extended the method to create images in using a fixed spatial distance between the source functions and the receive location.

SUMMARY OF EMBODIMENTS OF THE INVENTION

In some embodiments, methods for determining a mechanical parameter for a sample having a target region using shear wave displacement includes: a) generating at least one shear wave with an excitation pulse in the target region at an excitation position; b) transmitting tracking pulses in a tracking region, at least a portion of which is outside the target region; c) receiving corresponding echo signals for the tracking pulses in the tracking region; d) repeating steps A through C for one or more additional excitation positions within the target region, wherein at least two of the excitation pulses overlap and the tracking region associated with each excitation position overlaps with the tracking region associated with at least one other excitation position; and e) determining at least one mechanical parameter of the target region based on at least one parameter of a shear wave displacement from two or more excitation pulses whose excitation positions are in the target region and whose associated tracking regions overlap outside the target region.

In some embodiments, the method includes transmitting and receiving one or more tracking pulses prior to one or more of the shear wave excitations. At least two shear waves may be generated in the target region by ultrasound push beams that overlap by between 5% and 75% of a lateral beamwidth.

In some embodiments, at least one parameter of the shear wave displacement comprises a leading edge of the shear wave displacement measured at a point in the tracking region outside of the target region.

In some embodiments, the at least one parameter of the shear wave displacement comprises a first time difference between the leading edges of the shear wave displacement between two shear waves generated in the target region, measured at a point in the tracking region outside the target region.

In some embodiments, determining the mechanical property comprises using a linear regression of the parameters of at least three shear waves in the target region.

In some embodiments, determining the mechanical parameter comprises determining the mechanical parameter from parameters measured at more than one point in the tracking region outside of the target region, and averaging or using a median operation for estimates of the mechanical parameter to output a final estimate.

In some embodiments, the shear waves and tracking regions comprise multiple valid target sub-regions with tracking regions outside of each sub-region, the method comprising processing each sub-region independently to form a set of estimates defining an array.

In some embodiments, the method includes defining the multiple sub-regions by the depth into the material, resulting in a 1-D array of estimates.

In some embodiments, the method includes defining the multiple sub-regions using lateral positions of the generated shear waves and the depth into the material, resulting in a 2-D image.

In some embodiments, the multiple sub-regions are defined by lateral and elevational positions of the generated shear waves and depth into the tissue, resulting in a 3-D volume.

In some embodiments, a spatial gradient of the parameter of the generated shear waves is used to determine the mechanical parameter of each voxel in the target volume.

In some embodiments, the mechanical parameter is a shear wave speed and is found by investing a magnitude of the spatial gradient.

In some embodiments, the mechanical parameter is a shear wave speed, and is found from the inverse of the radial component of the gradient, relative to the tracking region.

In some embodiments, the at least one mechanical parameter includes at least one of shear elasticity modulus, Young's modulus, storage modulus dynamic shear viscosity, shear wave velocity and mechanical impedance of the target region.

In some embodiments, the target region comprises an in vivo human tissue sample.

In some embodiments, the target region comprises in vitro biomaterials.

In some embodiments, the echo signals of the sample are detected with an internally inserted ultrasound probe array.

In some embodiments, the echo signals of the sample are detected with an externally applied ultrasound array.

In some embodiments, the shear waves are generated with an applied shear wave source comprising an ultrasound transducer and/or mechanical vibrator.

In some embodiments, the shear waves comprise a displacement that is orthogonal to a direction of the first and shear waves.

In some embodiments, computer program product for determining a mechanical parameter for a sample having a target region using shear wave displacement is provided, the computer program product comprising a non-transient computer readable medium having computer readable program code embodied therein, the computer readable program code comprising: computer readable program code configured to: a) generate at least one shear wave with an excitation pulse in the target region at an excitation position; b) transmit tracking pulses in a tracking region, at least a portion of which is outside the target region; c) receive corresponding echo signals for the tracking pulses in the tracking region; d) repeat steps a) through c) for one or more additional excitation positions within the target region, wherein at least two of the excitation pulses overlap and the tracking region associated with each excitation position overlaps with the tracking region associated with at least one other excitation position; and computer readable program code configured to determine at least one mechanical parameter of the target region based on at least one parameter of a shear wave displacement from two or more excitation pulses whose excitation positions are in the target region and whose associated tracking regions overlap outside the target region.

The computer program code may be configured to carry out the ultrasound method described herein.

In some embodiments, an ultrasound system for determining a mechanical parameter for a sample having a target region using shear wave displacement is provided. The system includes: an ultrasound transducer array; a controller configured to control the ultrasound transducer array, the controller comprising: a shear wave generator configured to generate at least one shear wave with an excitation pulse in the target region at an excitation position; a signal analyzer configured to transmit tracking pulses in the target region at a tracking position; to receive corresponding echo signals for the tracking pulses at the tracking position in the target region, and to determine at least one mechanical parameter, wherein the system is configured to carry out the method described herein.

BRIEF DESCRIPTION OF THE DRAWINGS

The accompanying drawings, which are incorporated in and constitute a part of the specification, illustrate embodiments of the invention and, together with the description, serve to explain principles of the invention.

DETAILED DESCRIPTION OF EMBODIMENTS OF THE INVENTION

Figure 1A:
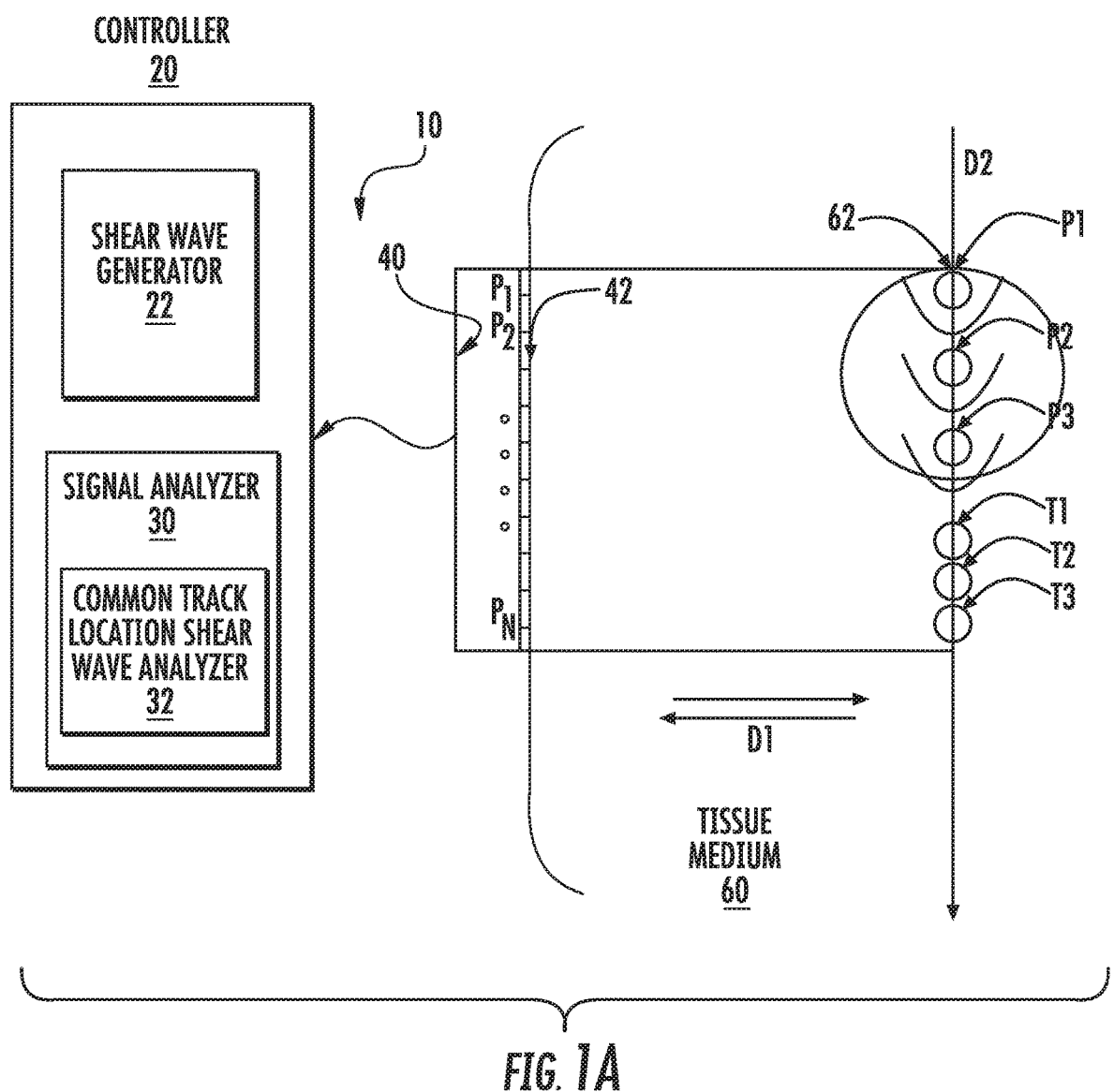
FIG. 1A is a schematic diagram of ultrasound systems, methods and computer program products according to some embodiments.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will frilly convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. For example, the term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

Embodiments according to the present invention are described herein with reference to the term "tissue." It will be understood that the term tissue can include biological materials, such as, blood, organs, vessels, and other biological objects found in a body. It will be further understood that embodiments according to the present invention may be applicable to humans as well as other species. Embodiments according to the present invention may also be utilized to image objects other than tissue.

It will be understood that the scope of the present invention includes, for example, two dimensional (2D) ultrasound imaging and 3D (or volumetric) ultrasound imaging. In addition, the components of the ultrasound imaging described herein may be packaged as a single unit or packaged separately and interconnected to provide the functions described herein.

Embodiments according to the present invention are also described by reference to Acoustic Radiation Force Imaging (ARFI) which is described in greater detail, for example, in U.S. Pat. No. 6,371,912, the entire disclosure of which is incorporated herein by reference. An acoustic radiation force may be used to apply a force to tissue thereby causing the tissue to move in the direction of the force and/or to generate a shear wave.

As used herein, a "shear wave" is a form of sample displacement in which a shear wave source, such as ultrasound energy, is transmitted into the sample in one direction and generates an extended shear wave that propagates in another direction that is substantially orthogonal to the direction of the shear wave source. The displacement caused by a shear wave source may be in a range between about 0.1 µm and about 300 µm. Other displacements can be provided.

The term "time of arrival" refers herein to the measured elapsed time between the transmission of a transmitting signal and the return of a corresponding reflected signal. The time of arrival is measured by conventional measurement techniques.

As illustrated in FIG. 1A, an ultrasound system 10 includes a controller 20, a signal analyzer 30 and an ultrasound transducer array 40. The ultrasound transducer array 40 may include a plurality of array elements 42 at positions $P_1$ through $P_N$. The array elements 42 are configured to transmit and receive ultrasound signals, and may be contacted to a target medium such as a tissue medium 60. As illustrated, the tissue medium 60 includes a target region 62. The ultrasound array 40 may include ultrasound array elements 42 that define transmit/receive locations for transmitting and receiving ultrasound signals along a direction D1. In some embodiments, the array 40 may be configured to transmit sufficient ultrasound energy, for example, by applying an impulse excitation acoustic radiation force to the medium 60 (commonly referred to as a "push" beam), to generate a shear wave that propagates in a direction D2 that is orthogonal to D1. The array 40 may also be configured to interrogate the tissue medium 60, for example, using ARFI or B-mode imaging techniques to monitor the tissue through time before and/or after the shear wave excitation force has been applied. ARFI imaging is discussed in U.S. Pat. Nos. 6,371,912; 6,951,544 and 6,764,448, the disclosures of which are hereby incorporated by reference in their entireties. Shear waves are discussed in U.S. Pat. Nos. 8,118,744 and 6,764,448, the disclosures of which are hereby incorporated by reference in their entireties. The ultrasound transducer array 40 may be a one-dimensional array configured to generate two-dimensional images or the ultrasound transducer array 40 may be a two-dimensional array configured to generate three-dimensional images.

The controller 20 may include a shear wave generator 22 and the signal analyzer 30 may include a common track location shear wave analyzer 32. The shear wave generator 22 and the common track location shear wave analyzer 32 may be configured to control the array 40 and/or to analyze echo signals received by the array 40 as described herein. The shear wave generator 22 and the common track location shear wave analyzer 32 may include hardware, such as control and/or analyzing circuits, and/or software stored on a non-transient computer readable medium for carrying out operations described herein.

The shear wave generator 22 and the common track location shear wave analyzer 32 may determine a mechanical parameter for the target region 62 of the sample tissue 60 by generating and analyzing a plurality of shear waves from a common track location. As used herein, the term "single track location" refers to a track location that detects parameters for multiple shear waves and is used interchangeably with the term "common track." Multiple common tracking locations may be used. As shown in FIGS. 1A and 2, the shear wave generator 22 may generate a first shear wave in the target region 62 at a first excitation source position P1 (Block 100; FIG. 2). The controller 20 can control the array 40 to emit tracking pulses in a region outside of the target region 62 at a tracking position T1 that is in a propagation direction D2 of the first shear waves (Block 102; FIG. 2). Corresponding echo signals for the tracking pulses at the tracking position T1 are received by the array 40 (Block 104; FIG. 2). The steps at Blocks 100, 102 and 104 may be repeated for second and third shear waves at respective second and third excitation positions P2 and P3 and tracking positions T2 and T3, respectively. Although three shear waves and three tracking positions are depicted in FIG. 1, it should be understood that any number of shear waves and tracking positions may be used, and the number of shear waves may also be different from the number of tracking positions. The common track location shear wave analyzer 32 determines at least one mechanical parameter of the target region 62 based on at least one parameter of a shear wave displacement from each of the at least the first, second, and third shear waves displacing tissue at the tracking positions T1-T3 (Block 106; FIG. 2). As shown in FIG. 1A, a push region is an area that is bounded by the shape of each push beam (e.g., P1-P3), and the target region 62 is the area bounded by the leading edges of the constituent push regions, which is associated with the tracking region. The imaged region is the area over which the echo signals are beamformed, the propagation region is a subset of the imaged region that includes measurable propagating shear waves, which are outside of the push regions and inside of an amplitude cutoff distance after which the shear waves dampen and are not detectable. The tracking region is the intersection of the propagation regions for a given set of pushes that are associated with a target region, e.g., the tracking positions T1-T3.

Figure 1B:
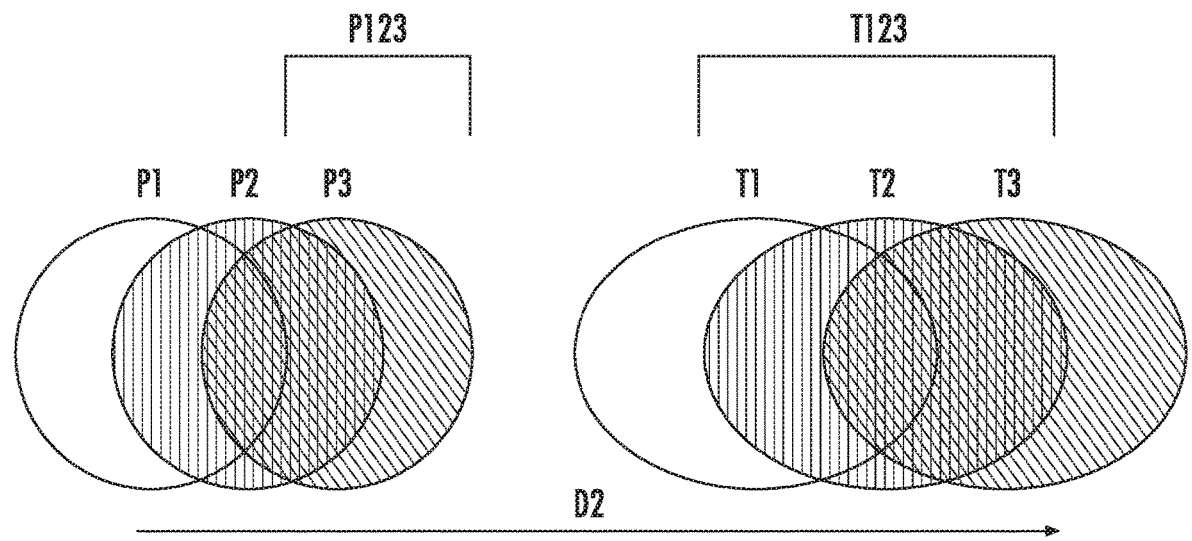
FIG. 1B is a schematic diagram of ultrasound excitation pulses and corresponding tracking signals according to some embodiments.
Figure 1C:
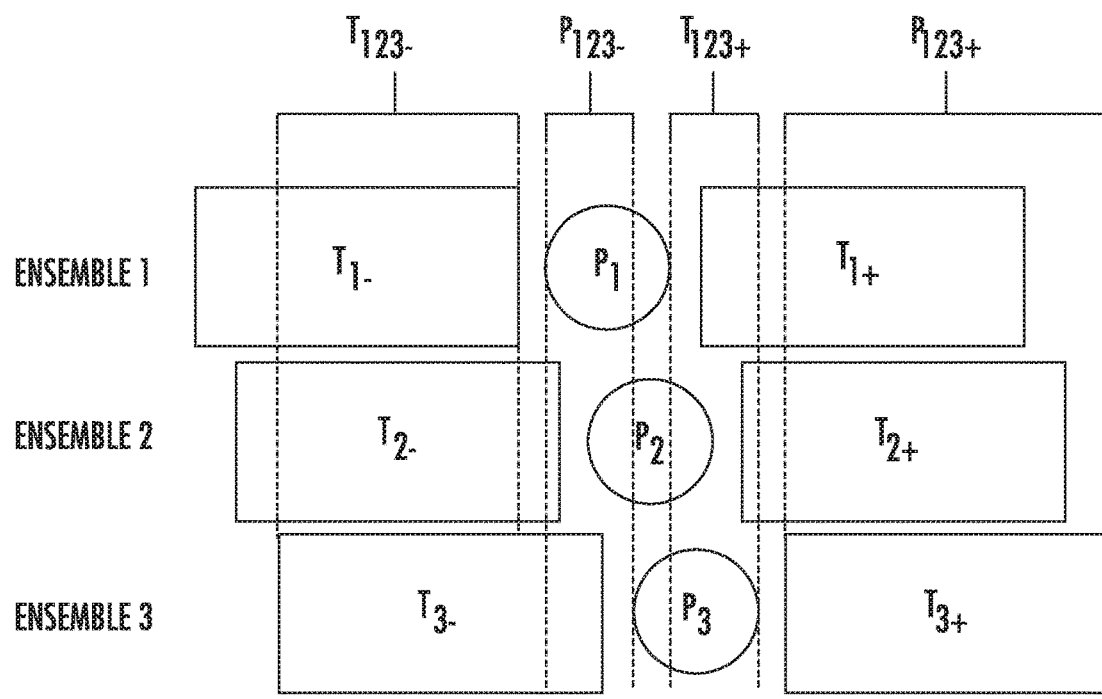
FIG. 1C is a schematic diagram of ultrasound excitation pulses and corresponding tracking signals according to some embodiments.
Figure 2:
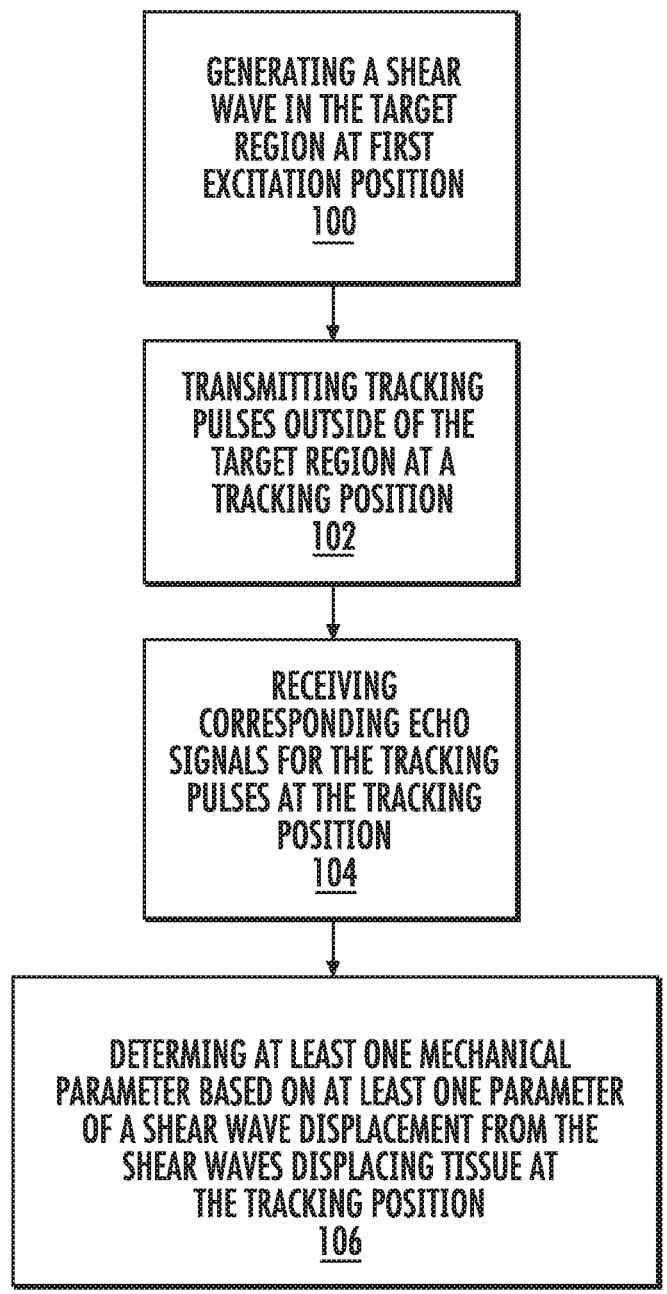
FIG. 2 is a flowchart illustrating operations according to some embodiments.

Although P1-P3 and T1-T3 are illustrated as spatially spaced apart positions in FIG. 1A, in some embodiments, the excitation positions P1-P3 and/or the tracking locations T1-T3 may overlap, as shown in FIG. 1B. Moreover, the tracking regions may be located outside of the pushing regions on either side of the pushing pulses as shown in FIG. 1C. As shown in FIGS. 1B-1C, the interrogation region P123 of the pushing pulses may include the leading edge of the resulting shear waves as detected in the tracking position T123. As shown in FIG. 1C, the interrogation region—P123 may be detected on an opposite side of the push pulses P1-P3 at the tracking position T123. Moreover, it should be understood that the pushing and tracking pulse sequence may be repeated such that any number of pushing and tracking pulses may be used. The overlap between the push pulses may be between 5% and 75% of the lateral beamwidth. The mechanical parameter can be determined from parameters measured at more than one point in the tracking region outside of the target region, and estimates of the mechanical parameter may be averaged or a median operation may be used to output a final estimate.

In some embodiments, the shear waves and tracking regions can include multiple valid target sub-regions with tracking regions outside of each sub-region and each sub-region may be processed independently to form a set of estimates defining an array. The multiple sub-regions may be defined by the depth into the material, resulting in a 1-D array of estimates; the multiple sub-regions may be defined using lateral positions of the generated shear waves and the depth into the material, resulting in a 2-D image; and/or the multiple sub-regions may be defined by lateral and elevational positions of the generated shear waves and depth into the tissue, resulting in a 3-D volume. A spatial gradient of the parameter of the generated shear waves may be used to determine the mechanical parameter of each voxel in the target volume in a 3-D volume. The mechanical parameter may be a shear wave speed and can be determined by estimating a magnitude of the spatial gradient. The mechanical parameter may be a shear wave speed, and can be found from the inverse of the radial component of the gradient, relative to the tracking region.

For example, the mechanical parameter may be based on a time of a peak displacement of tissue, an inflection in a displacement slope of tissue displacement at the tracking positions T1-T3 and/or a relative or absolute displacement amplitude of a shear wave displacement from the shear waves. In this configuration, the displacement of tissue due to multiple shear waves may be detected at a single or common tracking location. In some embodiments, the noise of the tracking signal may be reduced. For example, "speckle" noise typically results in ultrasound imaging due to the interference of the returning wave at the transducer aperture due to the distribution of scatterers within a resolution cell. Because the shape and position of the push beams used to generate the shear waves are defined by the absorption properties of the target medium and not by scattering, their relative positions are resistant to the speckle bias, which results in speckle noise when multiple tracking positions are used to determine a propagation of a shear wave. For any pair of recording locations away from a single source, the signals of tissue motion at each location will be time-delayed versions of one another, with the time-delay reflecting the shear wave velocity between the recording locations. Similarly, for any pair of source excitations, the tissue motion signals recorded at any single or common location outside of the sources will be time-delayed versions of one another with the time delay reflecting the shear wave velocity between the source locations.

Figure 3A:
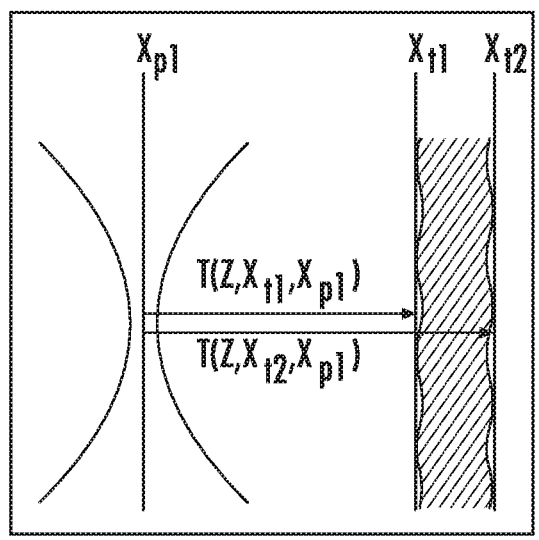
FIGS. 3A-3B are diagrams of arrival times for a single shear wave at two track locations (FIG. 3A) and for two shear waves at a single track location (FIG. 3B) according to some embodiments.
Figure 3B:
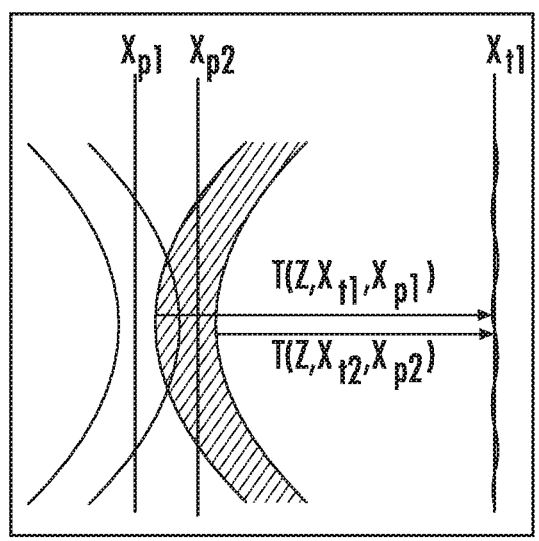

As illustrated in FIGS. 3A-3B, the "pushing" and "tracking" beams and their positions along the axis of propagation are denoted with $x_p$ and $x_t$, respectively. FIG. 3A illustrates the shear wave velocity reconstruction using conventional shear wave imaging in which the propagation of a shear wave is detected at two track locations. FIG. 3B illustrates two shear waves that are generated and tracked at a single shear wave track location. As shown in FIG. 3B, the tissue motion signals recorded at any single location outside of the sources will be time-delayed versions of one another with the time delay reflecting the shear wave velocity between the source locations. The locations of the beams $x_p$ and $x_t$ are typically determined by electronic steering and focusing from an array of ultrasonic elements. For the three-dimensional version, the positions of the push beams are described by $(x_p, y_p)$ and the track beams by $(x_t, y_t)$. These coordinates are defined at each depth z, and may vary with z if the beams are steered relative to one another.

Figure 4:
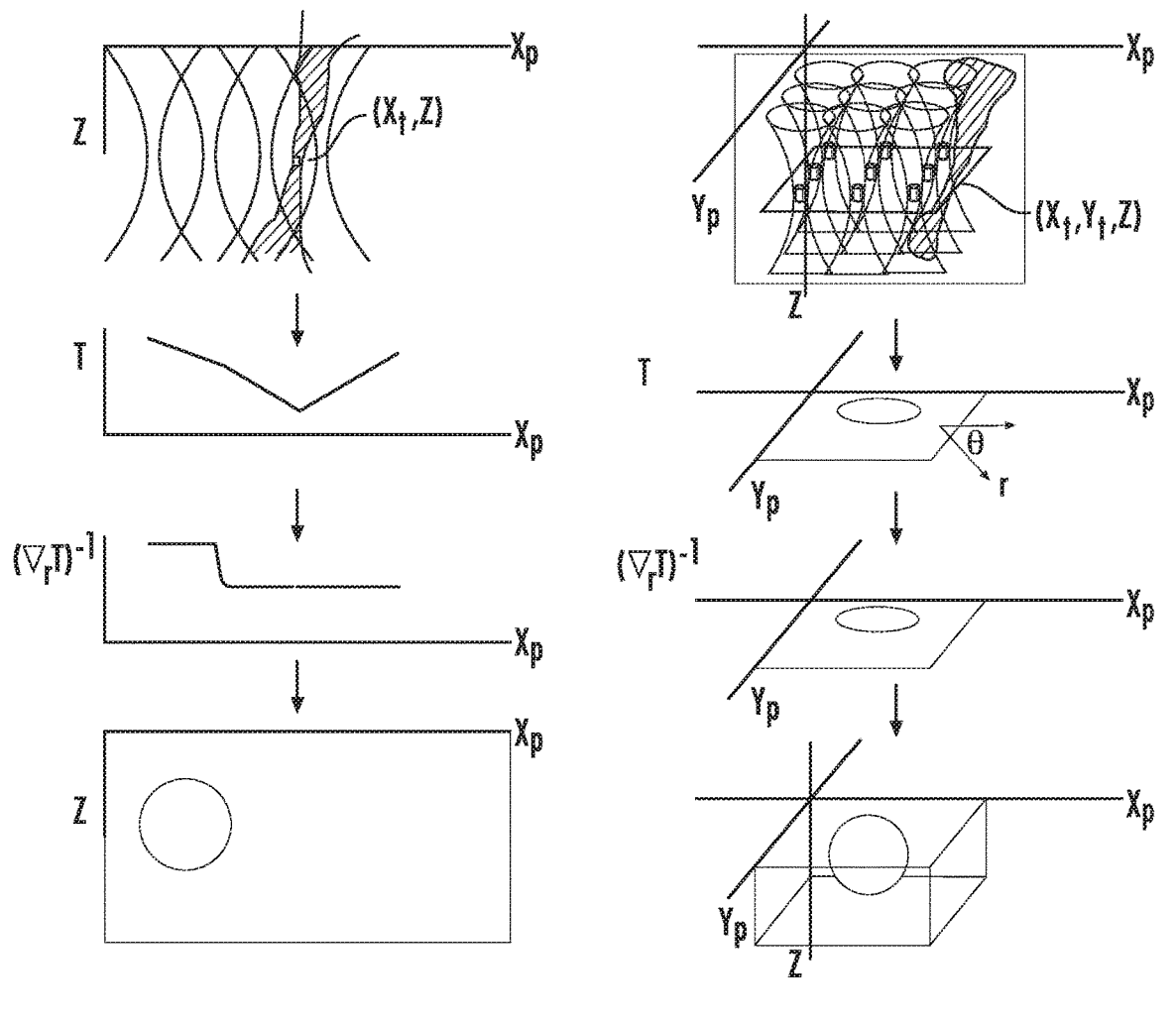
FIG. 4 is a diagram of the single track location shear wave elastic imaging (STL-SWEI) in two dimensions (left side) and three dimensions (right side) according to some embodiments.

A diagram of the method is shown in FIG. 4 for both the 2D single track location-shear wave elasticity imaging (STL-SWEI) (left side sequence) and 3D STL-SWEI (right side sequence). In the 2D STL-SWEI on the left side of FIG. 4, a plurality of pushes are sequentially delivered at positions $x_p$, tracking the response at one or more locations $x_t$ for each push, in line with the pushing locations. A characteristic time of flight is found between the push locations, relative to the track location. The inverse of the gradient of arrival time $(\nabla rT)^{-1}$ is estimated as the slope of T, with the sign determined by the position relative to the tracking location $x_t$. In the 3D STL-SWEI diagram on the right side of FIG. 4, an image is made by combining the profiles from multiple depths within the depth of field. The sequence is similar to the 2D, but the tracking beam does not need to be aligned with the push beams. The position of the track beam is found experimentally, and $(\nabla rT)^{-1}$ is calculated relative to the tracking location.

A number of non-mutually exclusive permutations on the method are possible:

1) The push beam grid is formed by translating a focused ultrasound transducer while holding the tracking transducer fixed.
2) The push beam grid is formed by electronically steering a matrix array transducer.
3) The push beam grid is generated sequentially, one push beam at a time.
4) The push beam grid is generated using multiple simultaneous pushes.
5) The axial field of view is extended by using multiple pushes focused at different depths.
6) The output is a single measurement at a point.
7) The output is an image.
8) The output is a volume.
9) The measurement is reported as shear wave speed (m/s).
10) The measurement is reported as shear modulus (kPa).
11) The measurement is reported as Young's Modulus (kPa).
12) The measurement is reported as complex viscoelastic parameters (i.e. $\mu1$ and $\mu2$).
13) A single output (point/image/volume) is generated from a single track beam.
14) Multiple outputs (points/images/volumes) are generated from multiple track beams and combined to increase the field of view.
15) Multiple outputs (points/images/volumes) are generated from multiple track beams and combined to suppress noise.
16) The characteristic time of flight is found as the time to peak displacement.
17) The characteristic time of flight is found as the time to peak velocity.
18) The characteristic time of flight is found by cross correlating the displacement profiles.
19) The characteristic time of flight is found by cross correlating the velocity profiles.
20) Shear wave speed $(\nabla rT)^{-1}$ is found relative to an assumed or known $(x_t, y_t)$.
21) Shear wave speed $(\nabla rT)^{-1}$ is found relative to a calculated $(x_t, y_t)$.
22) Shear wave speed $(\nabla rT)^{-1}$ is found using $(\|\nabla T\|)^{-1}$.
23) Shear wave speed $(\nabla rT)^{-1}$ is found from a local linear regression of the time of flight.

In some embodiments, the at least one parameter of the shear wave displacement includes a leading edge of the shear wave displacement. For example, the at least one parameter of the shear wave displacement may include a first time difference between a leading edge of the shear wave displacement between at least the first and second shear waves and a second time difference between a leading edge of the shear wave displacement between at least the second and third shear waves. Determining at least one mechanical parameter of the target region based on at least one parameter of a shear wave displacement from each of the at least the first, second, and third shear waves displacing tissue at the tracking position may be performed by applying a linear regression of the first and second time differences. Without wishing to be bound by any particular theory, the tracking of the leading edge of the shear waves may reduce resolution limitations due to beam overlap. In some embodiments, sub push-beamwidth lateral resolution may be achieved by assigning values to correct positions on the curved wavefront as described herein. For example, the first, second and third shear waves may be overlapping shear waves, and in some embodiments may overlap by between 0 and 75% of the transmit beamwidth and/or have a spacing between 0.1 mm and 2 mm.

In addition, by using more than two push beams for each estimate of a shear wave parameter, such as shear wave velocity, a linear regression may be used. The size of the regression kernel may establish the trade-off between noise suppression and resolution improvement. Moreover, parallel receive beams may be used at the tracking location to make multiple estimates of the same region of interest, which can then be averaged together to further suppress the variance with little to no corresponding reduction in resolution. In some embodiments, the push beams may have a 75% overlap or more (0.16 mm spacing or more) to make the image with no resolution degrading regression of filtering.

The shear waves may be generated simultaneously at Block 100, but must be generated sequentially when using overlapping beams, with separate tracking ensembles for each push as illustrated in FIG. 1C and the positions T1, T2 and T3 may be in the propagation path of the shear waves generated by push pulses at the positions P1, P2 and P3 so that the shear waves arrive at positions T1, T2 and T3 at sequentially. Stated otherwise, for standard shear wave imaging, a pair of recording or tracking locations that are spaced apart from the shear wave source are used, such that the signals of tissue motion at each location will be time-delayed versions of one another with the time-delay reflecting the shear wave velocity between the recording locations. Similarly, in single tracking location detection, for any pair or set of three or more source excitations, the tissue motion signals recorded at any single location outside of the sources will be time-delayed versions of one another with the time delay reflecting the shear wave velocity between the source locations in a tissue region with substantially homogeneous tissue stiffness.

The tracking pulses may be used to determine at least one mechanical parameter of the target region 62, including a shear elasticity modulus, Young's modulus, storage modulus dynamic shear viscosity, shear wave velocity and mechanical impedance of the target region 62 using any suitable technique, including SWEI analysis techniques known to those of skill in the art.

In addition, it should be understood that more than two or three excitation sources may be used to generate a set of sequential shear waves that may be detected at a single tracking location. Moreover, an array of tracking locations may be used to detect corresponding sets of shear waves propagating through a single or common one of the tracking locations, and two-dimensional and three-dimensional images may be produced. It should be understood that the shear waves at the source excitation position P1, P2 and P3 may be generated with an ultrasound transducer and/or a mechanical vibrator. The excitation sources may transmit a displacement pulse sufficient to generate a shear wave in the region of interest.

The tracking signals may be detected and/or the shear waves may be generated repeatedly as described herein through a region of interest, for example, to generate an image. The tracking signals may be detected and/or the shear waves may be generated as described herein with an internally inserted ultrasound probe array or an externally applied ultrasound array. In some embodiments, the target region may be an in vivo human tissue sample; however, in vitro biomaterials, such as engineered tissues or hydrogels may be used.

The mechanical parameter(s) of the sample, such as shear elasticity modulus, Young's modulus, storage modulus dynamic shear viscosity, shear wave velocity and mechanical impedance, can be correlated to measurement of healthy/diseased tissue states, such as by using actual clinical data and known healthy/diseased tissue states. The clinical data can be based on other factors such as demographic information, e.g., age, gender and race, to correlate the measurement of the mechanical parameter(s) with a measurement of healthy/diseased tissue states in a particular demographic group.

In some embodiments, the mechanical parameter(s) of the sample can be monitored as a function of time by performing the shear wave analyzing techniques described herein on a sample repeatedly over a period of time. A healthy/diseased tissue state determination can be based on a change in the mechanical parameter(s) as a function of time. For example, the mechanical parameter(s) can be monitored over a period of minutes, hours, days, weeks, months or even years to determine the progression of the disease and/or the efficacy of treatment.

In some embodiments, the mechanical parameter(s) may be used to form an ultrasound image, such as a B-mode image or an ARFI image.

Embodiments according to the present invention will now be described with respect to the following non-limiting examples.

Two Dimensional Imaging

Experimental Setup:

A custom Zerdine phantom (CIRS) was imaged with a prototype Siemens 12L4 linear array transducer connected to a Siemens Acuson SC2000 ultrasound scanner (Siemens Healthcare, Mountain View, Calif.). The phantom contained four stepped cylinder inclusions, with diameters of 1.5 mm, 2.5 mm 4 mm, 6 mm, and 10 mm. The cylindrical inclusions had nominal shear moduli G originally listed by CIRS as 0.67 kPa, 5.33 kPa, 8 kPa, and 10.67 kPa, and a background with G=2.67 kPa. Each combination of inclusion size and stiffness was imaged with six independent speckle realizations.

Pulse Sequences:

In order to maintain registration and to provide a closely-matched comparison between the three types of images without biasing the results in favor of one type, a pulse sequence was designed to acquire all three images in a single acquisition. A series of 400 cycle, 4.6 MHz excitation pulses, focused at 25 mm with an F-number of 2, were sequentially delivered every 0.167 mm (¼ of the lateral beamwidth) across a 20 mm lateral field of view. Two 5 MHz tracking frames were recorded before each excitation and 40 tracking frames were recorded after each excitation, at a frame rate of 10,000 fps to image the induced shear waves. For each excitation location, the sample was excited three times with different tracking configurations. Tracking lines were recorded at the excitation, and with 0.167 mm spacing to either side of the excitation, offset between 1.3 mm and 6.5 mm from the excitation, for a total of 32 lines to the left, one in line with, and 32 lines to the right of each excitation.

Image Formation and Post-Processing:

For each type of elasticity image, Loupas's algorithm was used with a 1.2 mm (4λ) kernel to estimate axial displacement relative to an anchored reference frame prior to excitation. See T. Loupas et. al. "Experimental evaluation of velocity and power estimate for ultrasound blood flow imaging by means of a two-dimensional autocorrelation approach," IEEE Trans. Ultrason., vol. 42, no. 4, pp. 672-688). For both STL-SWEI and MTL-SWEI ("multi track location" SWEI), the displacements were differentiated through tracking time ("slow time") at each pixel and band-pass filtered with a 3rd order Butterworth filter with cutoff frequencies of 50 and 1000 Hz. The filtered axial velocities were next fed through a directional filter for each push location (MTL-SWEI) or track location (STL-SWEI) to remove reflection artifacts. The axial velocities were each median filtered axially with a 0.54 mm kernel. The arrival time of the shear wave at each location was found from the peak of the velocity signal at each pixel, using quadratic subsample estimation, and excluding candidate estimates representing velocities far outside the expected range (greater than 6 m/s or less than 0.5 m/s). A moving lateral linear regression was applied around each sample, with varying kernel sizes from 0.16 mm (2-sample difference) to 4 mm (26-sample regression). For MTL-SWEI, each of the 126 push locations formed a 10.4 mm wide sub-image from all of the track beams associated with it. The same is true of STL-SWEI, but each sub-image represents a single track location and the pushes within 5.2 mm to either side. For the STL-SWEI images, an additional depth-dependent lateral shift was applied to each sub-image to compensate for the shape of the push beam. Each sub-image was then laterally cropped to the center 6 mm, since velocity estimates with greater than 3 mm separation between the push and track beams had low displacement SNR; this also served to avoid boundary effects when using large kernel sizes. Finally, the 126 cropped sub-images for each mode were aligned and combined by taking the median at each aligned pixel across the resulting 20 overlapping estimates.

Figure 5A:
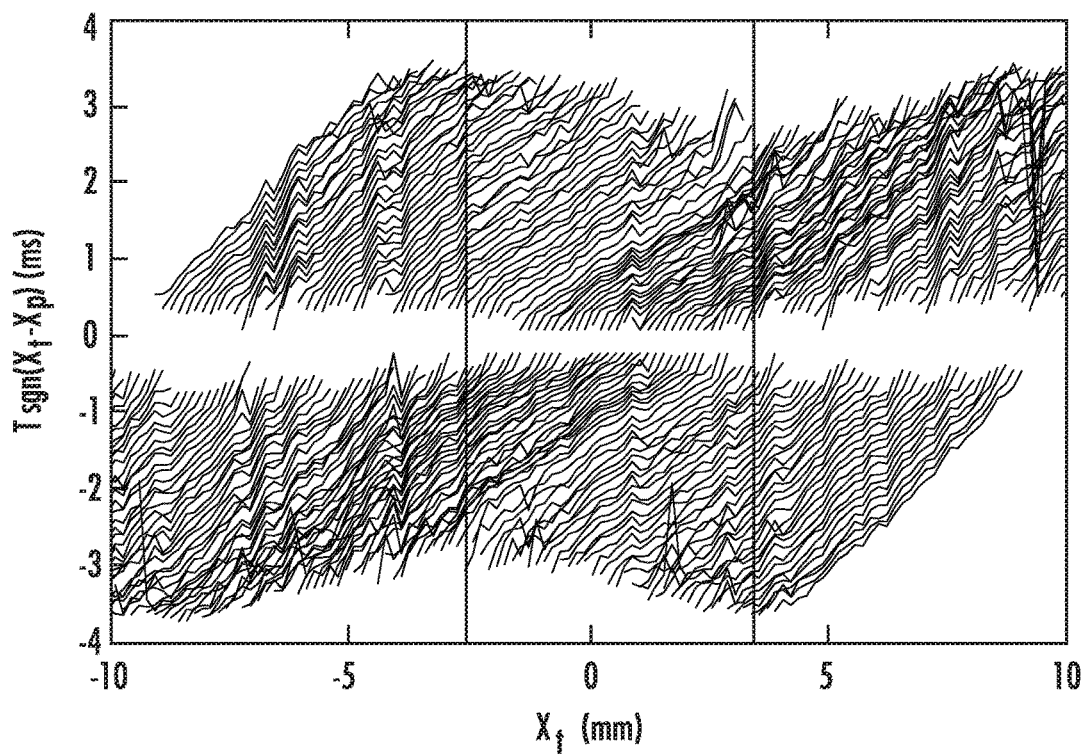
FIG. 5A is a graph of arrival times for multiple-track location SWEI (MTL-SWEI).
Figure 5B:
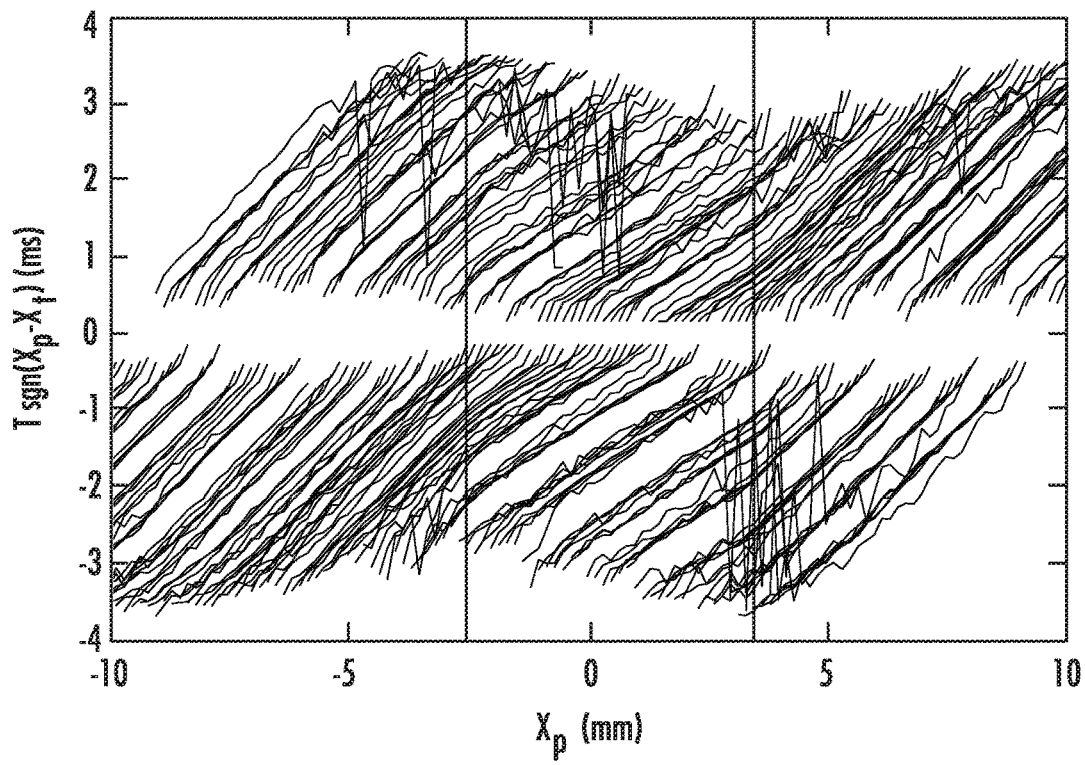
FIG. 5B is a graph of arrival times for STL-SWEI according to some embodiments.

Image Comparison:

The MTL-SWEI and STL-SWEI arrival times for the Type IV (GqEI=6.48 kPa) inclusions are shown in FIGS. 5A-5B, which highlights the speckle-reduction properties of STL-SWEI. FIG. 5A illustrates arrival times for MTL-SWEI and FIG. 5B illustrates arrival times for STL-SWEI according to some embodiments. In FIGS. 5A-5B, the arrival times are shown across the center of the Type IV ($G_{qEI}$=6.48 kPa) for a 6 mm inclusion. The vertical bars indicate the inclusion boundary, and arrival times that are measured to the left of the push have been negated to improve readability. The speckle bias is apparent in FIG. 5A processing as shown in the waviness in the slope of the lines. The speckle bias in the STL-SWEI of FIG. 5B, however, is a constant offset to each line, which does not affect slope estimation. The slope of each arrival time line is much more smooth in STL-SWEI, allowing for visual recognition of the region of elevated stiffness in the center, appearing as a decreased slope.

Figure 6:
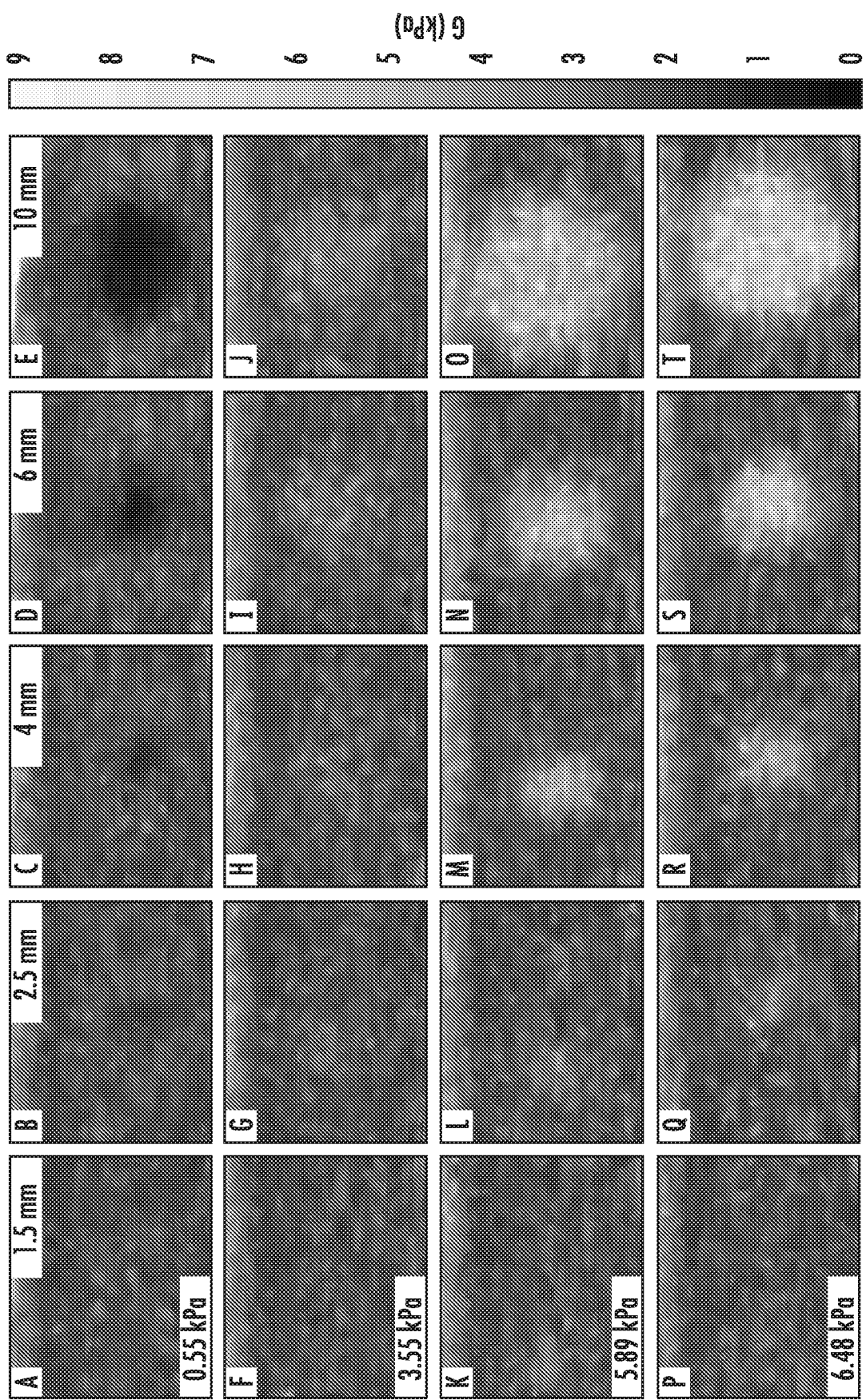
FIG. 6 shows images for various indicated size and stiffness targets for MTL-SWEI (prior art).
Figure 7:
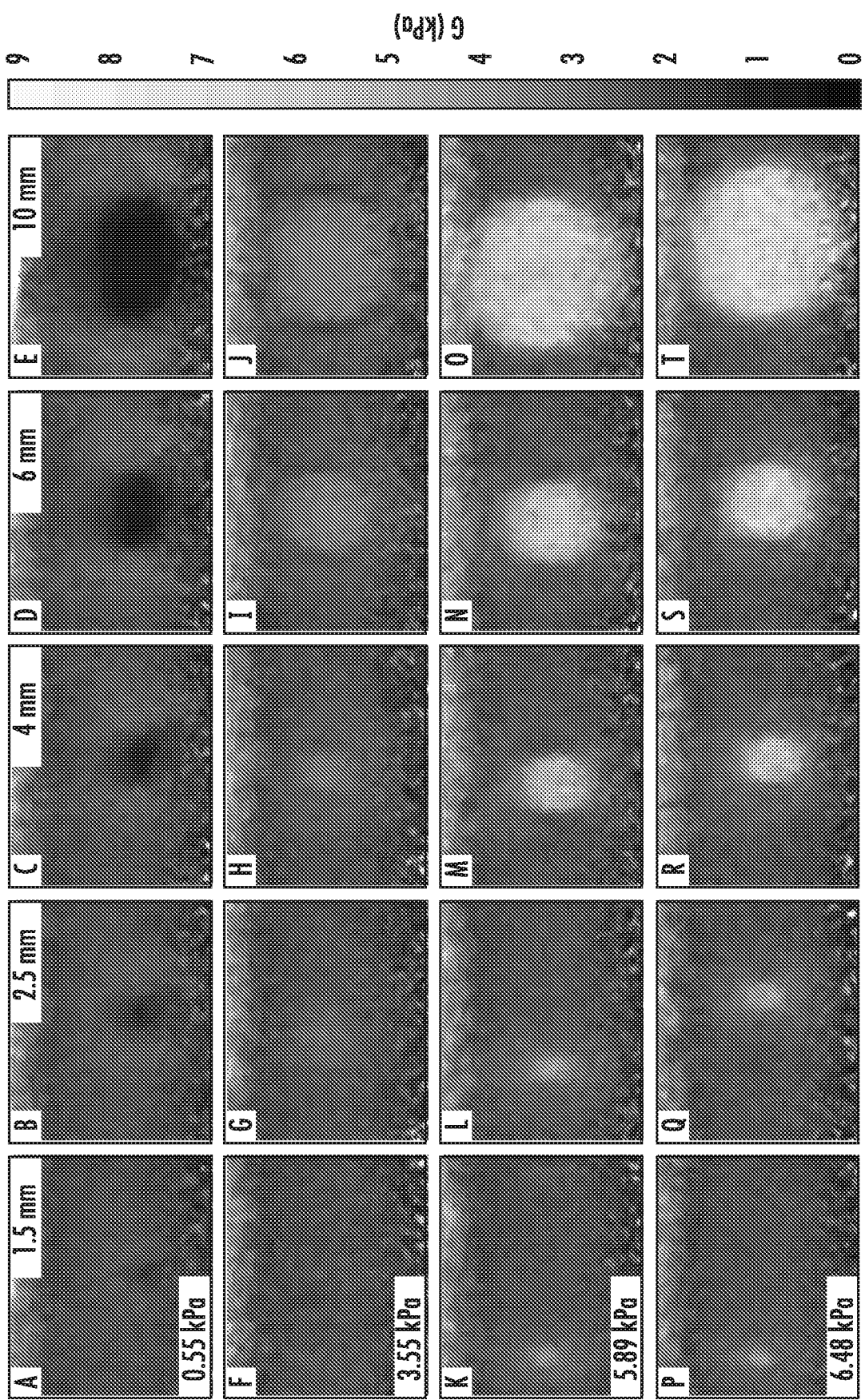
FIG. 7 shows images for various indicated size and stiffness targets for STL-SWEI according to some embodiments.

Images showing each combination of size and stiffness lesion are shown in FIGS. 6 and 7, in which a 0.33×0.33 mm median filter has been applied to the final images and reduced noise is shown. Values are shown as shear modulus G, with a dynamic range of 0 to 9.3 kPa, though the same images can be made directly from shear wave speed. ARFI images have an equivalent dynamic range, at 0 to 4 times the normalized inverse background displacement value. For the MTL- and STL-SWEI images, the image shown is the median value of shear modulus G for all overlapping estimates within 3 mm of the excitation, which translates to 20 estimates for each pixel. In each set of images, lesion conspicuity increases with lesion size and contrast.

Figure 8:
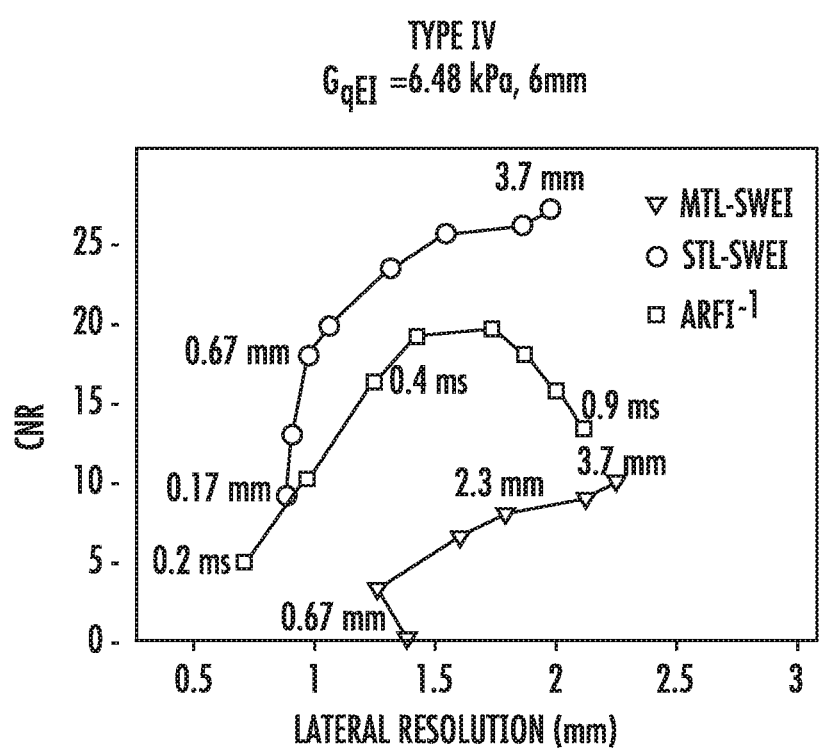
FIG. 8 is a graph of the contrast-to-noise-ratio (CNR) and resolution tradeoff curves for STL-SWEI and MTL-SEI for the Type IV, 6 mm inclusions, and ARFI according to some embodiments.

6 mm Inclusions: CNR Vs Resolution:

For the 6 mm diameter, Type IV inclusion, CNR is plotted against lateral resolution in FIG. 8. This plot portrays the "trade-off curves" between system resolution and CNR for each of the imaging modalities, based on post-processing variables. The points on the trade-off curve for ARFI show different values of time step, starting at 0.2 ms after the excitation in the bottom left, and incrementing each 0.1 ms to the right, with the highest CNR achieved at 0.5 ms. The points on the STL-SWEI and MTL-SWEI curves indicate different regression filter kernel sizes, with better CNR and worse resolution associated with larger kernels. STL-SWEI shows the best combinations of CNR and resolution, though ARFI achieves finer resolution for the 0.2 ms time step. The height and width of the semitransparent gray ovals show the standard deviation of each measurement over the six acquisitions.

Figure 9:
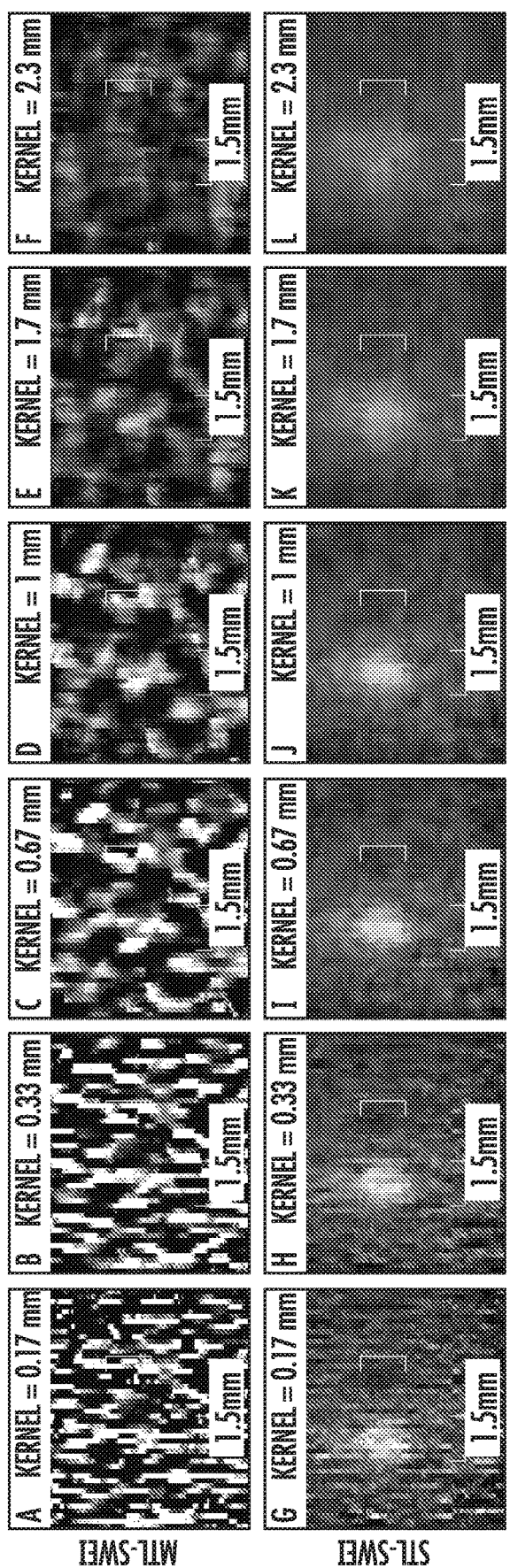
FIG. 9 shows images of MTL-SWEI (images A-F) and STL-SWEI (images G-L) of the 1.5 mm, Type IV inclusion at different regression filter values according to some embodiments.

1.5 mm Inclusions:

CNR vs Resolution: The tradeoff of different regression kernels is visualized in FIG. 9 for the 1.5 mm, Type IV inclusion. In the top row of images in FIG. 9, MTL-SWEI fails to visualize the lesion effectively, with high noise associated with small kernels and low contrast associated with large kernels. In the bottom row of images in FIG. 9, STL-SWEI clearly shows the lesion with the correct size, trading resolution for noise suppression from left to right and eventually losing contrast as the kernel size exceeds the target size.

Figure 10:
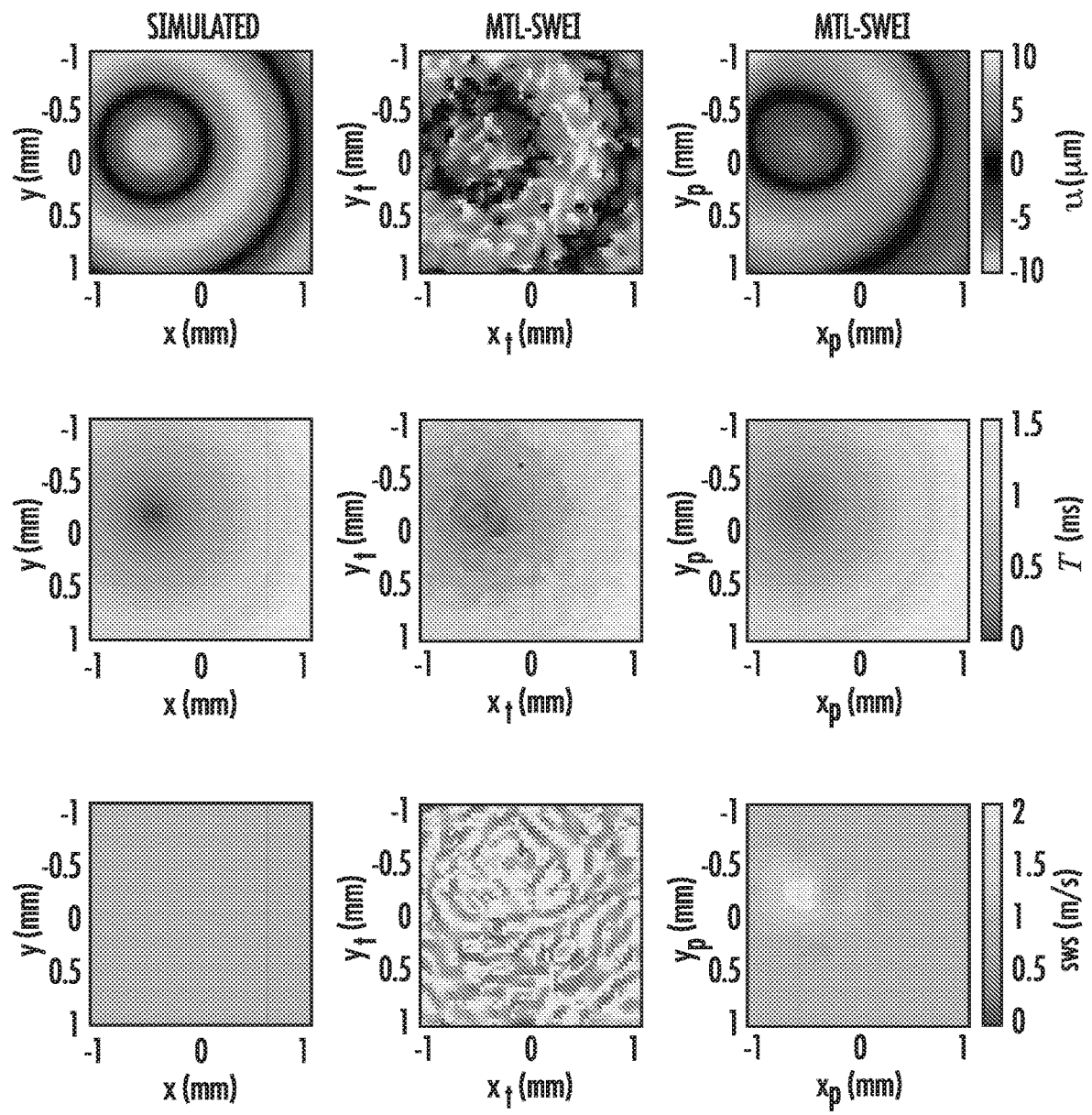
FIG. 10 illustrates MTL- and STL-SWEI displacement frames (top row), corresponding arrival times (middle row) and shear wave speed images (bottom row) according to some embodiments.

The top row of FIG. 10 shows a single frame captured at a single depth for the simulated motion, MTL-SWEI, and STL-SWEI. The push and track location, respectively are labeled for MTL-SWEI and STL-SWEI. MTL-SWEI is much noisier than STL-SWEI. The middle row shows the arrival times estimated from the top row. The speckle bias is seen in the MTL-SWEI as spatially correlated over- and under-estimation. The STL-SWEI estimates are more smooth, but are centered away from $(x_t, y_t)$, with the offset indicating the biased position of the track beam, as labeled. Detecting and correcting the speckle bias are key for creating very high resolution shear wave imaging at clinical depths. The bottom row shows the corresponding shear wave images. While MTL-SWEI is on average accurate, it requires spatial smoothing to be usable. STL-SWEI on the other hand, appears more precise and accurate, only failing in the immediate vicinity of the push, where shear propagation assumptions may break down.

3 Dimensional

To extend STL-SWEI to three-dimensions, the position of the pushing beam may be adjusted independent of one or more tracking beams. Indeed, a 3D STL-SWEI image could be made from a single element tracking piston.

A diagram of a 3D STL-SWEI algorithm is shown in the right side of FIG. 4. Note how the tracking beam is not aligned with the push beams such that any voxel in the tracking field of view will reconstruct the plane of pushes at its depth, regardless of orientation (some component of the induced displacement must be detected at that voxel, so a perpendicular tracking beam is not likely to work without lateral tracking). Once the grid of pushes has been excited and recorded, each tracking voxel (in the case of parallel beamforming) in the plane of pushes is processed separately. When indexed by push location, a C-scan synthetic shear wave is created at each voxel, with the shear wave radiating out from the tracking voxel's position.

The displacements may then be filtered in the axial, temporal, tracking or pushing dimensions. A characteristic arrival time is computed for each sample, and the inverse of the gradient magnitude serves as an estimate of the shear wave velocity.

Figure 11:
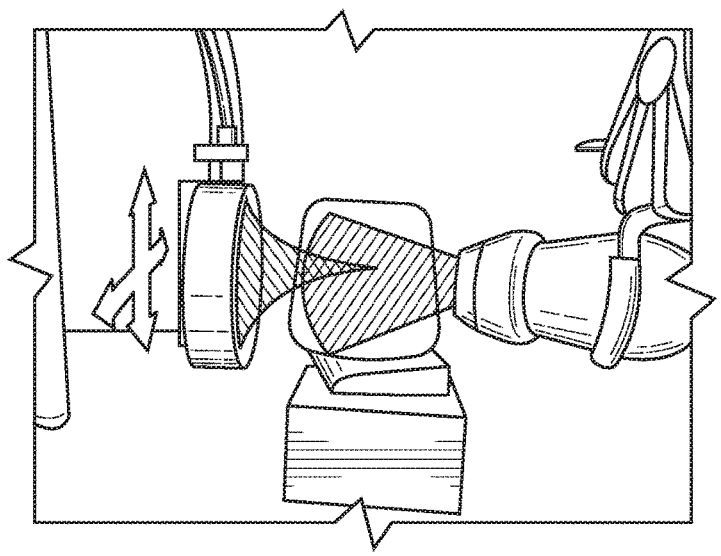
FIG. 11 is a digital image of an experimental setup with a concave HIFU piston moved with a translation stage to steer the push beam while a 4ZIC matrix array transducer tracks the displacement from the opposite side of the sample according to some embodiments.
Figure 12A:
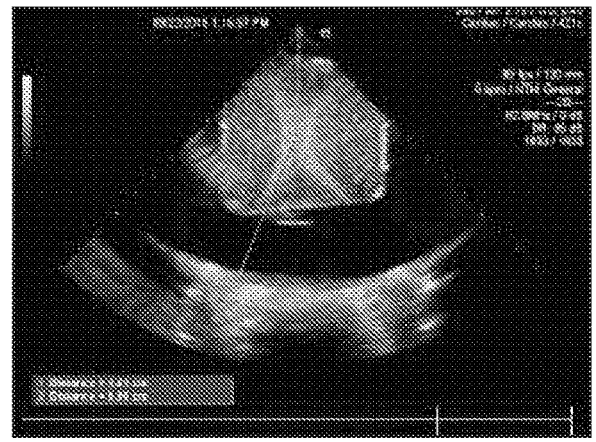
FIG. 12A is a two-dimensional B-mode image of the experimental set up of FIG. 11.
Figure 12B:
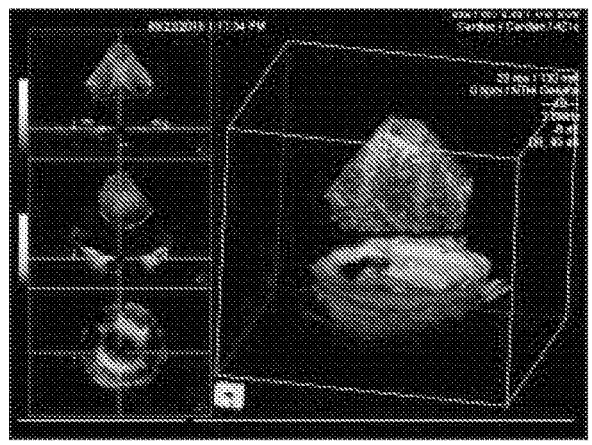
FIG. 12B is a three-dimensional B-mode image of the experimental set up of FIG. 11.

Experimental Setup:

A concave 1.1 MHz HIFU piston ((H-101, Sonic Concepts, Bothell, Wash.) was mounted to a translation stage, pointing sideways at the target phantom, and a Siemens 4z1c matrix array ultrasound transducer was positioned opposite the phantom (a uniform gelatin phantom created in lab, with a measured shear wave speed of 1.2 m/s), looking back through at the sample (FIG. 11). The HIFU piston has a fixed focal depth of 6 cm, which was aligned with the center of the phantom using the 4z1c's 2 and 3D B-modeon the Siemens SC2000 ultrasound scanner (Siemens Medical 2 Systems, Issaquah, Wa) (FIGS. 12A-12B). The HIFU piston was driven through a matching network and RF power amplifier (E&I A150, Electronics & Innovation, Rochester, N.Y.). For each push, a series of 96 128×8×8 voxel ultrasound volumes was recorded, between −8 degrees and +8 degrees in both the θ and φ directions, and 7 cm in depth, for a tracking volume rate of 6,250 vps. A diverging wave transmit was used, with the 64 beams formed on parallel receive. To drive the piston, a function generator sent a 300-cycle 1.1 MHz pulse 0.56 ms after it detected the beginning of each acquisition sequence, to coincide with the 5th volume in the sequence.

Image Formation and Post-Processing: Loupas's algorithm was used with a 1.5 mm (5λ) kernel to estimate axial displacement relative to an anchored reference frame prior to excitation. The displacements were band-pass filtered through tracking time ("slow time") at each voxel with a 3rd order Butterworth filter with cutoff frequencies of 50 and 1000 Hz.

The arrival time of the shear wave at each location was found from the peak of the displacement signal at each voxel, using quadratic subsample estimation, and excluding volumes below 2.5 ms after the push to exclude reverberation artifacts in the displacements. The gradient of arrival times was found in the $x_p$ and the $y_p$ dimensions and the shear wave speed was estimated as:

$$SWS = \frac{1}{\sqrt{(\nabla_{x_p} T)^2 + (\nabla_{y_p} T)^2}}$$

No spatial filtering was applied to any of the data at any stage (a 3×3 pixel kernel was needed for calculating the gradient).

Figure 13:
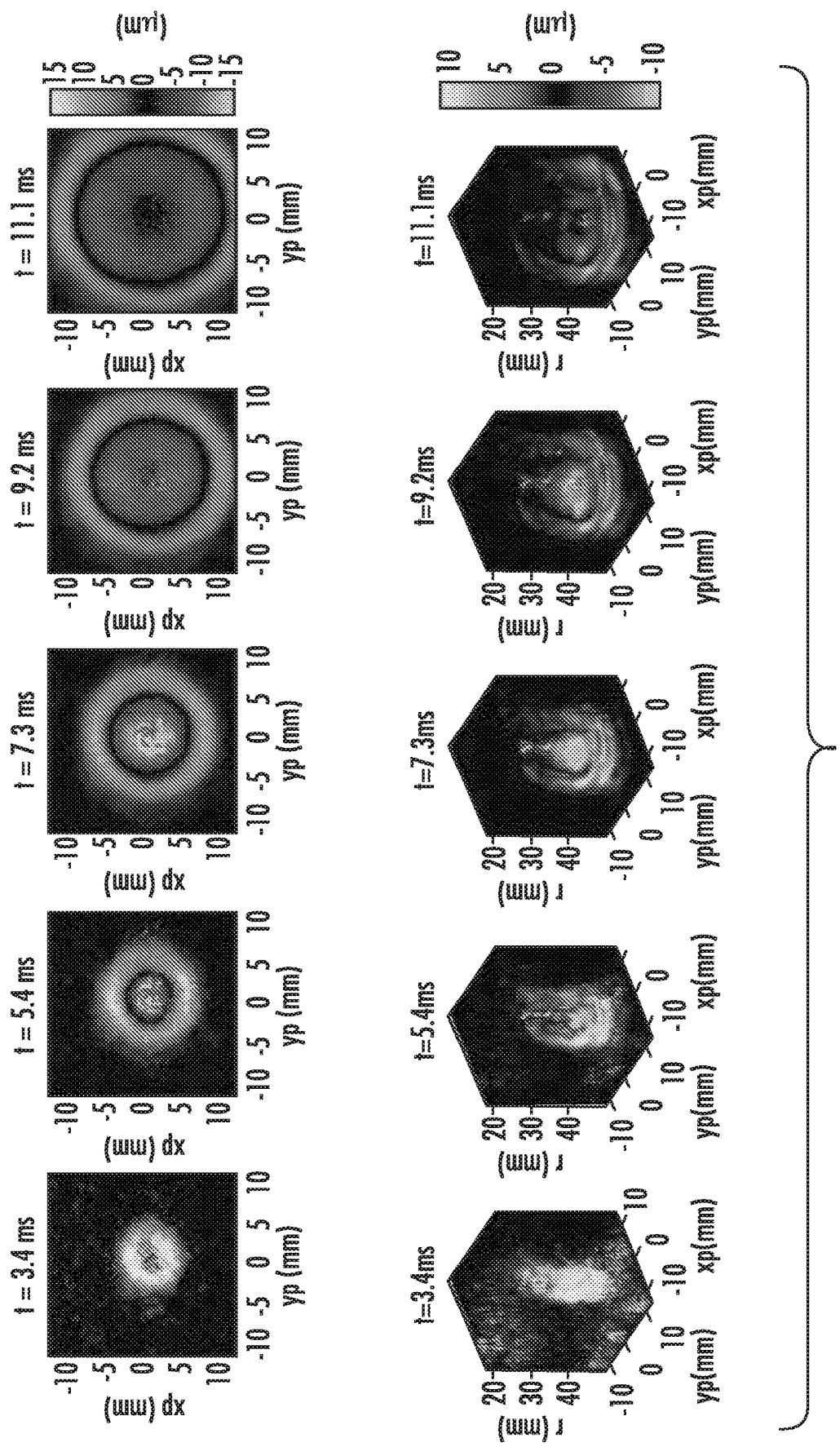
FIG. 13 shows images of C-scan frames (top row) and volumes (bottom row) from a three-dimensional STL-SWEI movie showing the shear wave propagation using the tracking voxel in the center of the tracking field of view at 4 cm according to some embodiments.

Results: Synthesized Shear Waves:

FIG. 13 shows 5 frames from the synthetic shear wave movie generated from a single voxel at 4 cm depth, steered in front of the 4z1c. Displacements have been negated for visual purposes, because the raw displacements were measured towards the 4z1c. The track voxel was positioned such that the shear wave radiates out from near the center of the grid, and propagation of the shear wave in the $x_p$ and $y_p$ dimensions is clear and smooth. The volume renders in the lower film strip pane help visualize the geometry of the push. The shape of the wavefront varies through depth, but the propagation is smooth.

Figure 14:
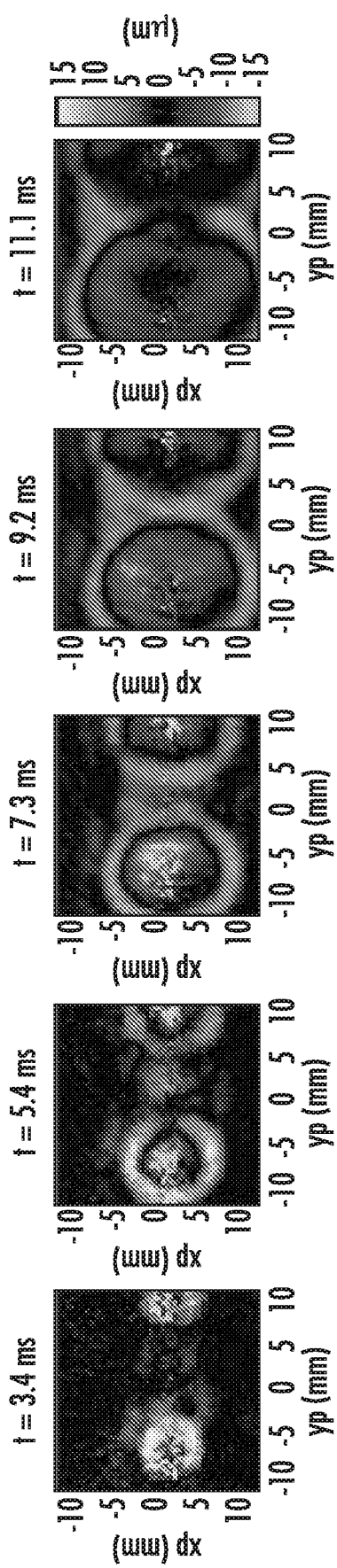
FIG. 14 shows images of C-scan frames from the three-dimensional STL-SWEI movie showing two shear waves propagating using a tracking beam voxel steered off-axis according to some embodiments.

FIG. 14 shows a different tracking voxel, positioned near the edge of the field of view, with a significant grating lobe. The tracking grating lobe appears as a secondary synthetic shear wave source, and the two synthetic waves interact around yp=4 mm, passing through one another.

Figure 15:
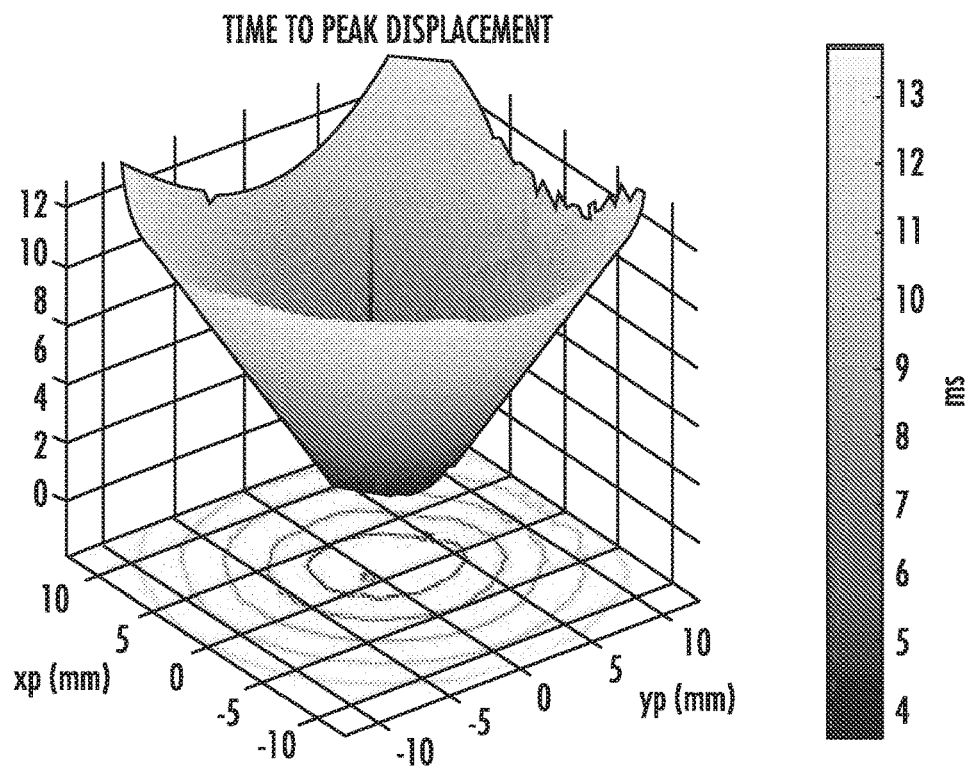
FIG. 15 is a graph of STL-SWEI arrival times in C-scan from the center tracking beam voxel according to some embodiments.
Figure 16:
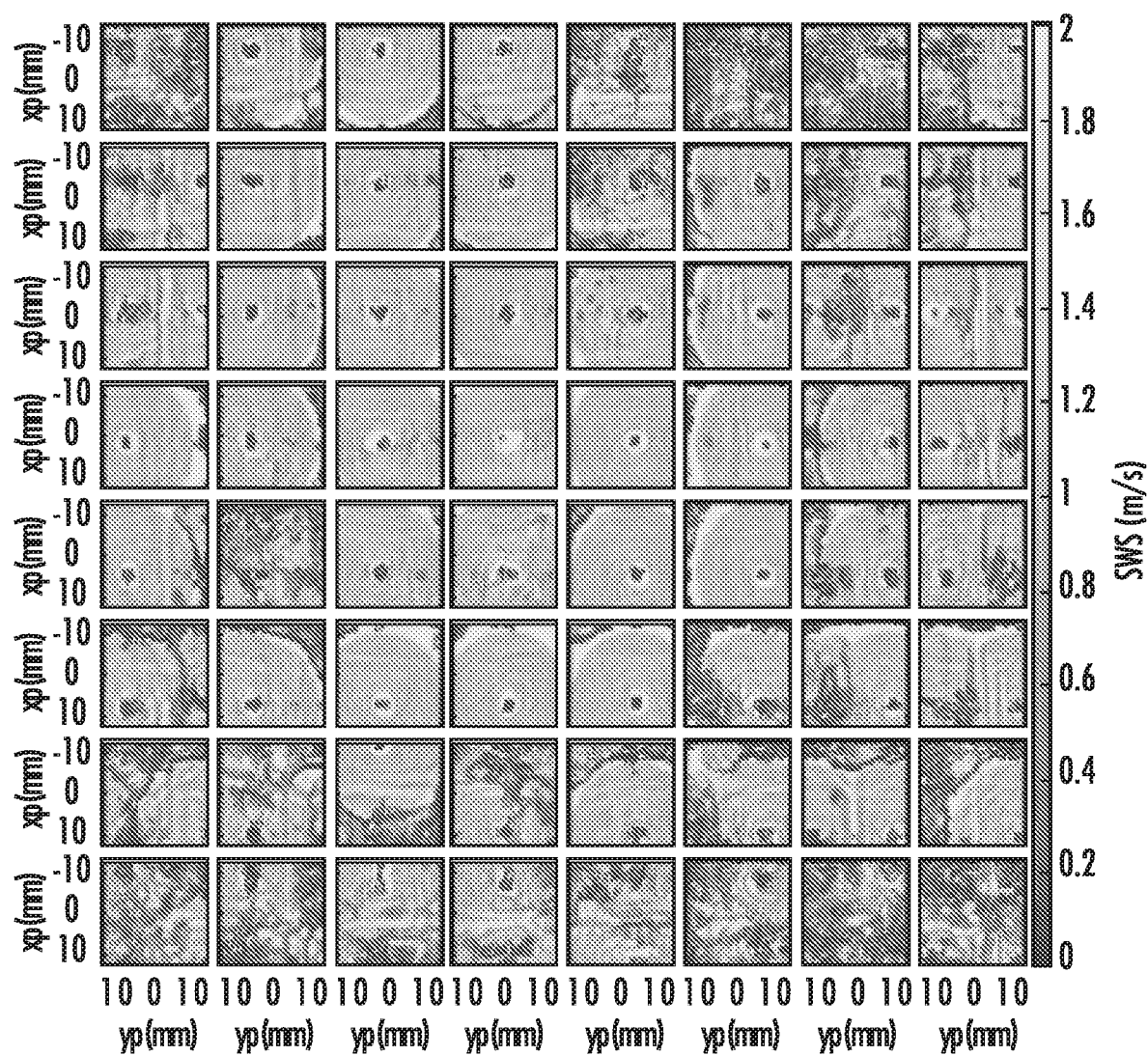
FIG. 16 shows images of estimated shear wave speed maps for each of the 64 tracking voxels at 4 cm depth in which steered voxels show corruption from grating lobes according to some embodiments.

Shear Wave Speed Estimation:

FIG. 15 shows the STL-SWEI arrival times in a c-scan computed at a depth of 40 mm at a surface, with projected contours. The shape of the cone is uniform, even with no spatial filtering. Only a few pixels in the middle, where the push and track beams align, show artifactual arrival times, but these regions are not typically used for shear wave speed estimation. FIG. 16 shows the shear wave speed maps for each of the 64 tracking voxels at 4 cm depth. No directional filters have been applied, so the interfering shear waves from grating lobes create artifacts in some of the track voxels, particularly those with more steering. Estimated wave speeds are also incorrect around the location of each of the track voxels (the sources of the synthetic waves), and at distances greater than 15 mm from the wave source, as the tracking time was not long enough to capture the peak. FIG. 8 shows the median shear wave speed map across the 64 voxels in FIG. 16 with no masking or exclusions. Even with a number of corrupted estimates, the map is smooth, representing a uniform shear wave speed of 1.16±0.05 m/s.

Speckle Elimination:

In some embodiments, the 3D STL-SWEI methods proposed herein have potential for generating quantitative elasticity volumes at very high resolutions. The reduction or elimination of speckle noise from the images creates a dramatic improvement in the smoothness of the arrival time maps over previous results with MTL-SWEI models over large spatial kernels to form viable estimates, but STL-SWEI needs no such inherent smoothing.

Figure 17:
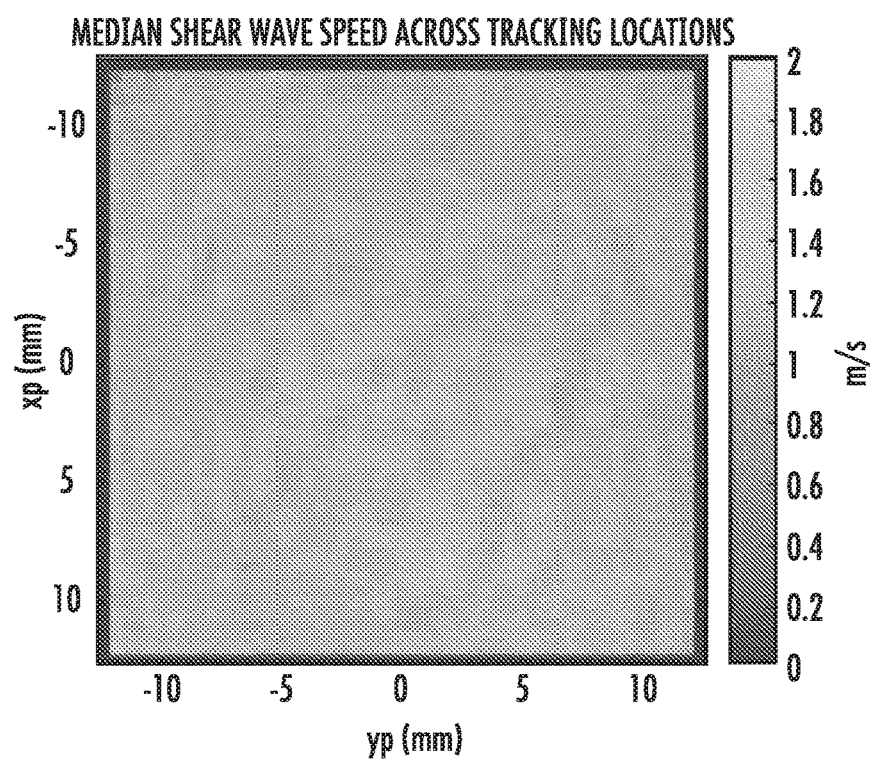
FIG. 17 is an image of the median shear wave speed map across all 64 voxels at 4 cm in which, on median, the artifacts from the grating, lobes and beam geometry are reduced or eliminated without any spatial filtering according to some embodiments.

Grating Lobes:

One of the effects shown herein is the effect of grating lobes in the tracking beams. Because the track beam is effectively imaging more than a single position at the same time, it creates a plurality of synthetic wave sources. When these wave sources interfere with one another, they disrupt the gradient of the arrival times, but this could be compensated for by finding the track location of the main lobe and applying a directional filter in cylindrical coordinates. The raw arrival times are used and simply averaged out the noise through the median across all the track beams. Indeed, the already low variation in FIG. 17 may be further reduced with such filters, or even simple weighted averaging. In fact, the grating lobes could even be used to provide extra maps, if their positions are detected and directionally filtered. For properly beam-formed beams, the maps appear of high quality. For these voxels, the matrix nature of the tracking array may be irrelevant as a focused piston could also record a full shear wave speed map.

Shear wave imaging has a number of clinical applications, as well as use in other material-characterization applications. STL-SWEI methods and systems described herein may allow for creation of higher resolution images than other methods. STL-SWEI may have the same acoustic exposure and frame rate limitations as ARFI imaging, but creates quantitative shear wave images. This improvement in resolution may be significantly valuable for imaging at clinically relevant depths. While the resolution of MTL-SWEI can be improved by using higher frequencies, these come at the expense of penetration. For STL-SWEI, lateral resolution may be improved without sacrificing penetration. This may be useful for imaging breast lesions, liver lesions and RF ablation lesions, or characterizing liver fibrosis, tissue engineered constructs, or myocardium. It also could be used in non-medical applications, such as characterizing the ripeness or cooked state of foods. In any case, STL-SWEI in 2D and 3D may enable accurate, high resolution imaging of the mechanical properties of a material.

The foregoing is illustrative of the present invention and is not to be construed as limiting thereof. Although a few example embodiments of this invention have been described, those skilled in the art will readily appreciate that many modifications are possible in the example embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for determining a mechanical parameter for a sample having a target region using shear wave displacement, the method comprising:
   a) generating at least one shear wave with an excitation pulse in the target region at an excitation position;
   b) transmitting a plurality of tracking pulses at one or more tracking positions in a tracking region, including at least one tracking position which is outside the target region;
   c) receiving corresponding echo signals for the plurality of tracking pulses in the tracking region;
   d) repeating steps a) through c) for two or more additional excitation pulses to provide a plurality at least three excitation pulses at two or more additional excitation positions within the target region, wherein each of the two or more additional excitation positions are different from one another and from the excitation position of the excitation pulse in step a) and the tracking region associated with each excitation position includes one or more shared tracking locations outside the target region that are shared by one or more tracking regions associated with the at least three excitation pulses; and
   e) determining at least one mechanical parameter of the target region based on at least one parameter of a plurality of shear wave displacements associated with the excitation pulses in the target region and detected at one or more of the shared tracking locations outside the target region.

2. There method of claim 1, further comprising transmitting and receiving one or more tracking pulses prior to one or more of the shear wave excitations.

3. The method of claim 1, wherein at least two shear waves are generated in the target region by ultrasound push beams that overlap by between 5% and 75% of a lateral beamwidth.

4. The method of claim 1, wherein at least one parameter of the shear wave displacement comprises a leading edge of the shear wave displacement measured at a point in the tracking region outside of the target region.

5. The method of claim 4, wherein the at least one parameter of the shear wave displacement comprises a first time difference between the leading edges of the shear wave displacement between two shear waves generated in the target region, measured at a point in the tracking region outside the target region.

6. The method of claim 1, wherein determining the mechanical property comprises using a linear regression of the parameters of at least three shear waves generated in the target region and detected at one of the shared tracking locations.

7. The method of claim 5, wherein determining the mechanical parameter comprises determining the mechanical parameter from parameters measured at more than one shared point in the tracking region outside of the target region, and averaging or using a median operation for estimates of the mechanical parameter to output a final estimate.

8. The method of claim 1, wherein the target region is a first target region of a plurality of target regions, and step d) comprises repeating steps a) through c) for one or more additional excitation positions outside the first target region, such that the plurality of excitation positions including the one or more additional excitations positions define additional target regions of the plurality of target regions, each target region defined by three or more excitation positions within a respective one of the plurality of target regions and with one or more shared tracking locations outside of the respective one of the target regions, the method comprising processing each of the plurality of target regions independently using one or more of its shared tracking positions to form a set of estimates defining an array, wherein at least some of the plurality of target regions share one or more excitation pulses.

9. The method of claim 8, further comprising defining the defining the plurality of target regions by the depth into the material, resulting in a 1-D array of estimates.

10. There method of claim 8, further comprising defining the defining the plurality of target regions using lateral positions of the generated shear waves and the depth into the material, resulting in a 2-D image.

11. The method of claim 8, further comprising defining the plurality of target regions by lateral and elevational positions of the generated shear waves and depth into the tissue, resulting in a 3-D volume.

12. The method of claim 11, further comprising calculating a two-dimensional spatial gradient of the parameter of the generated shear waves in the lateral and elevational dimensions or a three-dimensional spatial gradient of the parameter of the generated shear waves in the lateral, elevational, and axial dimensions to determine the mechanical parameter of each voxel in the target volume.

13. The method of claim 12, wherein the mechanical parameter is a shear wave speed and is found by estimating a magnitude of the spatial gradient.

14. The method of claim 12, wherein the mechanical parameter is a shear wave speed, and is found from the inverse of the radial component of the gradient, relative to the tracking region.

15. The method of claim 1, wherein the at least one mechanical parameter includes at least one of shear elasticity modulus, Young's modulus, storage modulus dynamic shear viscosity, shear wave velocity and mechanical impedance of the target region.

16. The method of claim 1, wherein the target region comprises an in vivo human tissue sample.

17. The method of claim 1, wherein the target region comprises in vitro biomaterials.

18. The method of claim 1, wherein the echo signals of the sample are detected with an internally inserted ultrasound probe array.

19. The method of claim 1, wherein the echo signals of the sample are detected with an externally applied ultrasound array.

20. The method of claim 1, wherein the shear waves are generated with an applied shear wave source comprising an ultrasound transducer and/or mechanical vibrator.

21. The method of claim 1, wherein the shear waves comprise a displacement that is orthogonal to a direction of the first and shear waves.

22. An ultrasound system for determining a mechanical parameter for a sample having a target region using shear wave displacement, the system comprising:
 an ultrasound transducer array;
 a controller configured to control the ultrasound transducer array, the controller comprising:
  a shear wave generator configured to generate at least one shear wave with an excitation pulse in the target region at an excitation position;
  a signal analyzer configured to transmit tracking pulses in the target region at a tracking position; to receive corresponding echo signals for the tracking pulses at the tracking position in the target region, and to determine at least one mechanical parameter, wherein the system is configured to carry out the method of claim 1.

23. The method of claim 1, wherein each of the successive excitation pulses has an identical tracking region comprises a plurality of shared track locations.

24. The method of claim 1, wherein the excitation pulse and the two or more additional excitation pulses are configured to transmit sufficient ultrasound energy to displace tissue and generate the shear wave.

25. A computer program product for determining a mechanical parameter for a sample having a target region using shear wave displacement, the method comprising, the computer program product comprising a non-transient computer readable medium having computer readable program code embodied therein, the computer readable program code comprising:
 computer readable program code configured to:
 a) generate at least one shear wave with an excitation pulse in the target region at an excitation position;
 b) transmit a plurality of tracking pulses at a plurality of tracking positions in a tracking region, including at least one tracking position which is outside the target region;
 c) receive corresponding echo signals for the plurality of tracking pulses in the tracking region;
 d) repeat steps a) through c) for two or more additional excitation pulses to provide a plurality at least three excitation pulses at two or more additional excitation positions within the target region, wherein each of the two or more additional excitation positions are different from one another and from the excitation position of the excitation pulse in step a) and the tracking region associated with each excitation position includes one or more shared tracking locations outside the target region that are shared by one or more tracking regions associated with the at least three excitation pulses; and
 computer readable program code configured to determine at least one mechanical parameter of the target region based on at least one parameter of a plurality of shear wave displacements associated with the excitation pulses in the target region and detected at one or more of the shared tracking locations outside the target region.

* * * * *